US009529649B2

(12) United States Patent
Boyle et al.

(10) Patent No.: US 9,529,649 B2
(45) Date of Patent: Dec. 27, 2016

(54) TECHNIQUES TO COMPUTE ATTRIBUTE RELATIONSHIPS UTILIZING A LEVELING OPERATION IN A COMPUTING ENVIRONMENT

(71) Applicant: SAS Institute Inc., Cary, NC (US)

(72) Inventors: Walter Boyle, Durham, NC (US); Cindy Ann Berry, Bluffton, SC (US)

(73) Assignee: SAS Institute Inc., Cary, NC (US)

( * ) Notice: Subject to any disclaimer, the term of this patent is extended or adjusted under 35 U.S.C. 154(b) by 0 days.

(21) Appl. No.: 14/920,264

(22) Filed: Oct. 22, 2015

(65) Prior Publication Data

US 2016/0117205 A1    Apr. 28, 2016

Related U.S. Application Data

(60) Provisional application No. 62/067,973, filed on Oct. 23, 2014.

(51) Int. Cl.
| G06F 9/54 | (2006.01) |
| G06Q 50/00 | (2012.01) |
| G06F 17/30 | (2006.01) |
| G06F 19/00 | (2011.01) |
| G06Q 50/24 | (2012.01) |
| G06Q 50/22 | (2012.01) |

(52) U.S. Cl.
CPC ......... *G06F 9/542* (2013.01); *G06F 17/30345* (2013.01); *G06F 19/32* (2013.01); *G06Q 50/22* (2013.01); *G06Q 50/24* (2013.01)

(58) Field of Classification Search
CPC ...................................................... G06F 19/32
See application file for complete search history.

(56) References Cited

U.S. PATENT DOCUMENTS 4,328,491 A    5/1982 Demetrescu et al.
4,491,725 A    1/1985 Pritchard
(Continued)

FOREIGN PATENT DOCUMENTS

WO    9512857 A1    5/1995

OTHER PUBLICATIONS

Symmetry Health Data Systems, Inc., "Proposal: Provider Risk Adjustment and Profiling," 54 pages, Jun. 12, 1994.
(Continued)

*Primary Examiner* — Brian W Wathen

(57) ABSTRACT

Various embodiments include a system having interfaces, storage devices, memory, and processing circuitry. The system may be coupled with one or more storage devices and may receive episode information for a patient from a storage device via one or more wired or wireless links, the episode information includes a plurality of episodes associated with the patient, each of the plurality of episodes is a specific instance of a medical condition. The system may generate a candidate episode pairs list comprising a plurality of candidate episode pairs. Embodiments may also include the system generating a transition list comprising episode pairs from the plurality of candidate episode pairs in the candidate episode pairs list and determining attribute relationships between the plurality of episodes for the patient based on episode pairs in the transition list, the attribute relationships used to attribute items between the plurality of episodes.

30 Claims, 29 Drawing Sheets

(56) References Cited

U.S. PATENT DOCUMENTS

| | | | |
|---|---|---|---|
| 4,667,292 A | 5/1987 | Mohlenbrock et al. | |
| 4,839,822 A | 6/1989 | Dormond et al. | |
| 5,001,630 A | 3/1991 | Wiltfong | |
| 5,018,067 A | 5/1991 | Mohlenbrock et al. | |
| 5,099,424 A | 3/1992 | Schneiderman | |
| 5,225,976 A | 7/1993 | Tawil | |
| 5,253,164 A | 10/1993 | Holloway et al. | |
| 5,301,105 A | 4/1994 | Cummings, Jr. | |
| 5,307,262 A | 4/1994 | Ertel | |
| 5,324,077 A | 6/1994 | Kessler et al. | |
| 5,325,293 A | 6/1994 | Dorne | |
| 5,365,425 A | 11/1994 | Torma et al. | |
| 5,483,443 A | 1/1996 | Milstein et al. | |
| 5,486,999 A | 1/1996 | Mebane | |
| 5,508,912 A | 4/1996 | Schneiderman | |
| 5,557,514 A | 9/1996 | Seare et al. | |
| 5,826,237 A | 10/1998 | Macrae et al. | |
| 5,835,897 A | 11/1998 | Dang | |
| 5,845,253 A | 12/1998 | Rensimer et al. | |
| 5,855,395 A | 1/1999 | Foote et al. | |
| 5,918,208 A | 6/1999 | Javitt | |
| 5,970,463 A | 10/1999 | Cave et al. | |
| 6,182,047 B1 | 1/2001 | Dirbas | |
| 6,223,164 B1 | 4/2001 | Seare et al. | |
| 6,370,511 B1 | 4/2002 | Dang | |
| 7,222,079 B1 | 5/2007 | Seare et al. | |
| 7,620,560 B2 | 11/2009 | Dang | |
| 7,725,333 B2 | 5/2010 | Dang | |
| 7,774,216 B2 | 8/2010 | Dang | |
| 8,340,981 B1* | 12/2012 | Cave | 705/2 |
| 8,639,528 B1* | 1/2014 | Cave | G06Q 10/10 705/2 |
| 2002/0165738 A1 | 11/2002 | Dang | |
| 2002/0173988 A1 | 11/2002 | Dang | |
| 2002/0173989 A1 | 11/2002 | Dang | |
| 2002/0173992 A1 | 11/2002 | Dang | |
| 2007/0021988 A1 | 1/2007 | Dang | |
| 2008/0021742 A1 | 1/2008 | Dang | |
| 2008/0059231 A1 | 3/2008 | Dang | |
| 2008/0306952 A1* | 12/2008 | Lynn | G06Q 10/00 |
| 2013/0006672 A1* | 1/2013 | Dang | G06F 19/328 705/3 |

OTHER PUBLICATIONS

Boyer, Nancy, "Case Mix Adjustment Using Claims Information to Drill Down Provider Profiling," HealthChex Inc., date unknown.
Gray, Michael, "Appraising Managed Healthcare's Quality," Managed Care, Summer 1991.
Health Chex, "Peer-A-Med Description of Products and Service", Aug. 1993.
"What is COT?" Course of Outpatient Treatment Marketing Brochure, Published by Medstat Inc., Date Unknown.
Keesey, Joan, et al., "The Episodes-of-Illness Processing System," A Rand Note, prepared for the U.S. Department of Health and Human Services, 75 pages, Jan. 1985.
Cave, Douglas, "Using Diagnostic Clusters to Evaluate Patterns of Treatment and Develop Capitation Rates," Employee Benefits Journal, vol. 20, No. 1, pp. 24-30, Mar. 1995.
Cave, Douglas, et al. "Pitney Bowes: Using Comprehensive Cost Information to Build Provider Networks," Benefits Quarterly, vol. 11, No. 2, pp. 19-25, Second Quarter (Jun.) 1995.
Cave, Douglas, "Profiling Physician Practice Patterns Using Diagnostic Episode Clusters," Medical Care, vol. 33, No. 5, pp. 463-486, May 1995.
Cave, Douglas, et al., "Case Study: Integrating Medical & Drug Claims Data," Pharmacare Economics, vol. 1, No. 1, pp. 30-38, Oct. 1996.
Mainous III, Arch G., et al., "Antibiotics for Colds in Children: Who are the High Prescribers?", American Journal of Diseases of Children, vol. 152, pp. 349-352, Apr. 1998.
Cave, Douglas G., "Pattern-of-Treatment Differences Among Primary Care Physicians in Alternative Systems of Care" Benefits Quarterly, 10(3):6-19, Third Quarter 1994.
Cave, Douglas G., "Small-Area Variations in the Treatment of Prevalent Medical Conditions: A Comparison of Three Cities in the Northeast," J. Ambulatory Care Manage, Aspen Publishers, Inc., vol. 18, No. 3: 42-57, 1995.
Cave, Douglas G., "Evaluating Health Plan Efficiency," Compensation & Benefits Management, vol. 8, No. 3, pp. 14-18, Summer 1992.
Cave, Douglas G., "Controlling Increases in the Volume and Intensity of Medical Services," Employee Benefits Journal, vol. 18, No. 2, pp. 11-18, Jun. 1993.
Cave, Douglas, et al., "Who Treats Medical Conditions More Cost Efficiently?" Medical Interface, vol. 7, No. 5, pp. 136-142, May 1994.
Cave, Douglas, et al., "Analyzing Patterns-of-Treatment Data to Provide Feedback to Physicians," Medical Interface, vol. 7, No. 7, pp. 117-128, Jul. 1994.
Cave, Douglas, "Analyzing the Content of Physicians' Medical Practices," J. Ambulatory Care Manage, vol. 17, No. 3, pp. 15-36, Jul. 1994.
"Advanced Profiling System Takes Center Stage in Capital Area Profiling Dispute," Medical Utilization Management, vol. 22, No. 14, Published by Faulkner & Gray, Dialog file 636, Accession No. 02452667, Jul. 21, 1994.
"'GMIS' Profiling System Pinpoints Total Costs," Medical Utilization Management, vol. 22, No. 17, Published by Faulkner & Gray, Inc., Dialog File 636, Accession No. 02520110, Sep. 8, 1994.
"New Episode-Building Software is a Hit in Provider Profiling Field," Medical Utilization Management, Published by Faulkner & Gray, Inc., Dialog File 636, Accession No. 02593104, Nov. 24, 1994.
Averill, Richard F., et al., "Design and Evaluation of a Prospective Payment System for Ambulatory Care," 3M Health Information Systems, Final Report, Dec. 31, 1990.
Collins, Linda J., "Managed Care May Improve Quality: Scrutiny Identifies Best Providers," Business Insurance, Feb. 19, 1990.
Garnick, D.W., et al., "Services and Charges by PPO Physcians for PPO and Indemnity Patients: An Episode of Care comparison," Medical Care, 28(10): 894-906, Oct. 1990.
Hibbard, Heddy, et al., "Conference Proceedings: Primary Care Research: Theory and Methods," U.S. Dept. of Health and Human Services, pp. 75-81, Sep. 1991.
Hornbrook, M.C., "Definition and Measurement of Episodes of Care in Clinical and Economic Studies," Cost Analysis Methodology for clinical Practice Guidelines Conference Proceedings, Grady, M.L. and Weis, K.A., eds., U.S. Dept. of Health and Human Services, Public Health Service, Agency for Health Care Policy and Research, AHCPR Publication 95-0001, Rockville, MD, pp. 15-40, Mar. 1995.
Hornbrook, M.C., et al., "Healthcare Episodes: Definition, Measurement and Use," Medical Care Review, vol. 42, No. 2, pp. 163-218, Fall 1985.
Kessler, L.G., et al., "Episodes of Psychiatric Utilization," Medical Care, vol. 18, No. 12, pp. 1219-1227, Dec. 1980.
Moscovice, I., "A Method for Analyzing Resource Use in Ambulatory Care Settings," Medical Care, vol. 15, No. 12, pp. 1024-1044, Dec. 1977.
Salkever, D.S., et al., "Episode-Based Efficiency Comparisons for Physicians and Nurse Practitioners," Medical Care, vol. 20, No. 2, pp. 143-153, Feb. 1982.
Schneeweiss, R., et al., "Diagnosis Clusters Adapted for ICD-9-CM and ICHPPC-2," The Journal of Family Practice, vol. 22, No. 1, pp. 69-72, 1986.
Smith, Norman, et al., "Establishing Fair Profiling Systems in a Managed Care Environment," Healthwise, 1994.
Weiner, Jonathan P., et al., "Development and Application of a Population-Oriented Measure of Ambulatory Care Case-Mix," Medical Care, vol. 29, No. 5, pp. 452-472, May 1991.

* cited by examiner

500

- IDENTIFY EPISODE INFORMATION FOR A PATIENT, THE EPISODE INFORMATION COMPRISING A PLURALITY OF EPISODES ASSOCIATED WITH THE PATIENT, EACH OF THE PLURALITY OF EPISODES IS A SPECIFIC INSTANCE OF A MEDICAL CONDITION
  505

- GENERATE A CANDIDATE EPISODE PAIRS LIST COMPRISING A PLURALITY OF CANDIDATE EPISODE PAIRS BY PERFORMING A CARTESIAN MERGE OF THE PLURALITY OF EPISODES AND COMPARING EACH OF THE CANDIDATE EPISODE PAIR WITH ASSOCIATION INFORMATION DEFINING RELATED MEDICAL CONDITIONS, EACH OF THE CANDIDATE EPISODE PAIRS HAVING A PARTICULAR ASSOCIATION LEVEL AND EACH OF THE CANDIDATE EPISODE PAIRS DEFINE A PARENT-CHILD RELATIONSHIP, EACH OF THE PARTICULAR ASSOCIATION LEVELS DEFINE A RELATIVE STRENGTH BETWEEN EPISODES IN A CANDIDATE EPISODE PAIR
  510

- GENERATE A TRANSITION LIST COMPRISING EPISODE PAIRS FROM THE CANDIDATE EPISODE PAIRS LIST OF CANDIDATE EPISODE PAIRS
  515

- DETERMINE HIERARCHAL RELATIONSHIPS BETWEEN THE PLURALITY OF EPISODES FOR THE PATIENT BASED ON THE EPISODE PAIRS IN THE TRANSITION LIST, THE HIERARCHAL RELATIONSHIPS USED TO DETERMINE ATTRIBUTE RELATIONSHIPS BETWEEN THE PLURALITY OF EPISODES
  520

*FIG. 5*

| Episode Parent | Episode Child | Episode Parent No. | Episode Child No. | Association Level | Start Day | End Day | Relationship Type | Offset |
|---|---|---|---|---|---|---|---|---|
| AMI | AMI | EA0506 | EA0506 | 2 | | | C | 1 |
| AMI | STR | EA0506 | EA0101 | 2 | | | C | 1 |
| STR | AMI | EA0101 | EP0520 | 3 | | | C | |
| STR | STR | EA0101 | EA0101 | 2 | | | C | 1 |
| KNRPL | STR | EA0510 | EA0101 | 4 | | | C | |
| KNRPL | AMI | EA0510 | EA0506 | 4 | | | C | |
| | | | | | | | | |
| | | | | | | | | |

| Episode ID | Member ID | Condition | Class | Episode Start Date | Trigger Date | Event Day(s) | Episode End Date |
|---|---|---|---|---|---|---|---|
| 1 | 001 | AMI | P | 9/2/2010 | x | x | 9/2/2010 |
| 2 | 001 | STR | P | 10/3/2011 | x | x | 10/6/2011 |
| 3 | 001 | KNRPL | P | 2/21/2014 | 1/2/2014 | x | 2/24/2014 |
| 4 | 001 | AMI | P | 2/22/2014 | 2/22/2014 | x | x |
| 5 | 001 | STR | P | 2/22/2014 | 2/22/2014 | x | x |

*FIG. 7*

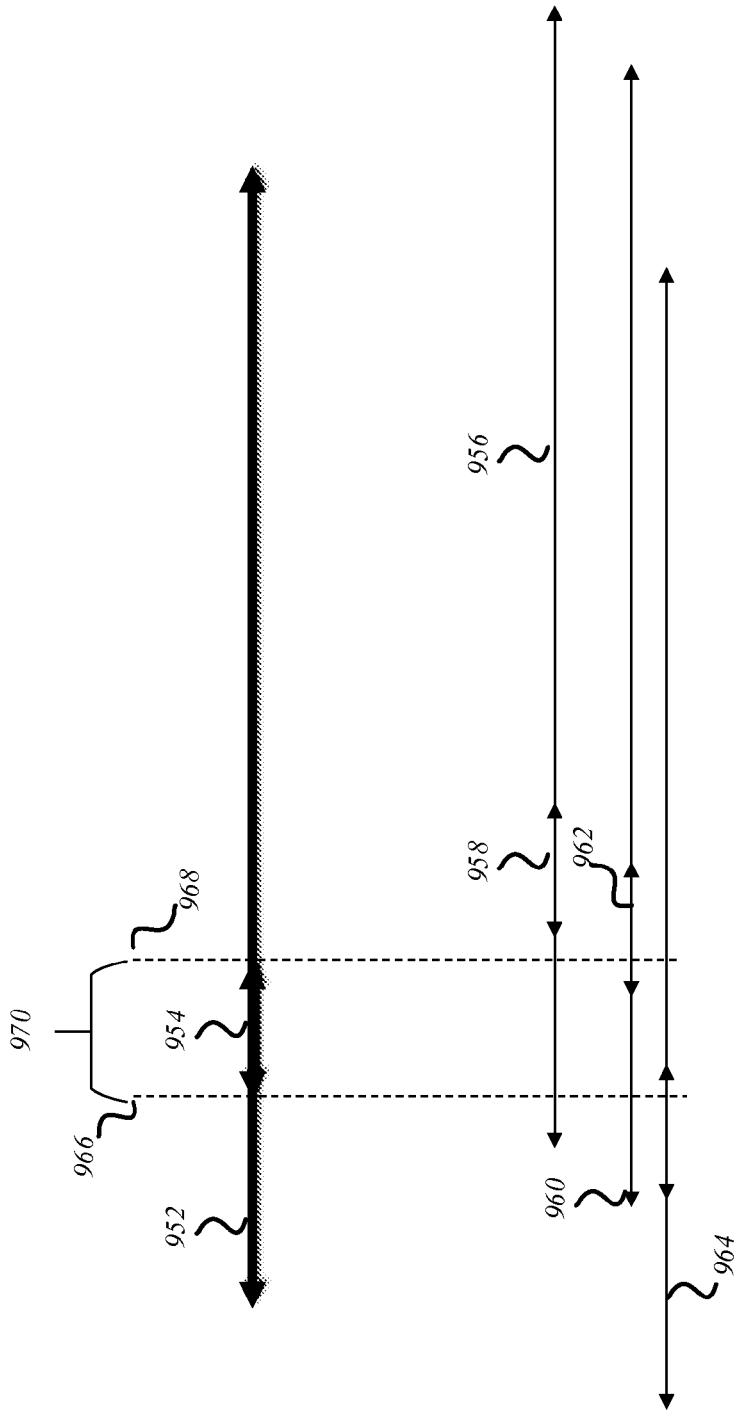

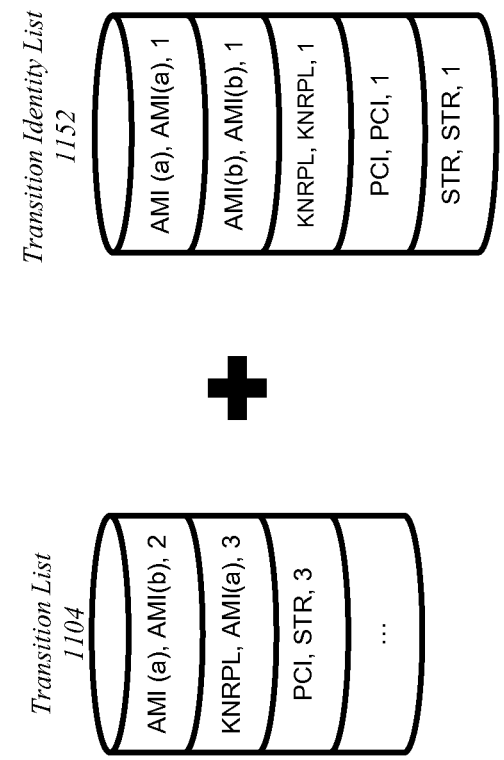
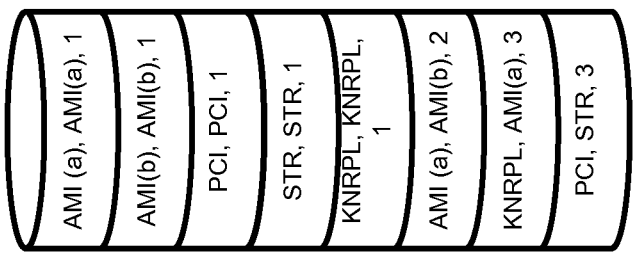
FIG. 11D

| Episode Child | Episode Final Parent | L1 | L2 | L3 | L4 | L5 | Comp. Flag |
|---|---|---|---|---|---|---|---|
| AMI(a) | AMI(a) | 1 | 1 | 0 | 0 | 0 | 0 |
| AMI(a) | KNRPL | 0 | 0 | 1 | 1 | 1 | 1 |
| AMI(b) | AMI(b) | 1 | 0 | 0 | 0 | 0 | 0 |
| AMI(b) | AMI(a) | 0 | 1 | 0 | 0 | 0 | 1 |
| AMI(b) | KNRPL | 0 | 0 | 1 | 1 | 1 | 1 |
| PCI | PCI | 1 | 1 | 0 | 0 | 0 | 0 |
| STR | STR | 1 | 1 | 0 | 0 | 0 | 0 |
| STR | PCI | 0 | 0 | 1 | 1 | 1 | 1 |
| KNRPL | KNRPL | 1 | 1 | 1 | 1 | 1 | 0 |

FIG. 12F

TECHNIQUES TO COMPUTE ATTRIBUTE RELATIONSHIPS UTILIZING A LEVELING OPERATION IN A COMPUTING ENVIRONMENT

RELATED APPLICATION

This application claims the benefit of priority of 35 U.S.C. §119(e) to U.S. Provisional Patent Application Ser. No. 62/067,973, filed on Oct. 23, 2014, which is incorporated by reference in its entirety.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

An apparatus includes processing circuitry coupled with memory. Further, the apparatus may include a candidate component having instructions storable in the memory and operable on the processing circuitry which may cause the candidate component to receive episode information for a patient from a storage device via one or more links, the episode information comprising a plurality of episodes associated with the patient, each of the plurality of episodes is a specific instance of a medical condition.

In some embodiments, the candidate component may also generate a candidate episode pairs list comprising a plurality of candidate episode pairs by performing a Cartesian merge of the plurality of episodes, and comparing each of the candidate episode pairs with association information defining related medical conditions. In embodiments, each of the candidate episode pairs may have a different association level and each of the candidate episode pairs define a parent-child relationship. Further, each of the association levels may define a relative strength between episodes in each of the candidate episode pairs.

An apparatus may also include a transition component having instructions storable in the memory and operable on the processing circuitry, the transition component can generate a transition list comprising episode pairs from the plurality of candidate episode pairs in the candidate episode pairs list.

The apparatus may also have a leveling component having instructions storable in the memory and operable on the processing circuitry to determine attribute relationships between the plurality of episodes for the patient based on episode pairs in the transition list, the attribute relationships used to attribute items between the plurality of episodes.

Embodiments may also include at least one non-transitory computer-readable storage medium may include instructions that when executed cause processing circuitry to identify episode information for a patient, the episode information comprising a plurality of episodes associated with the patient, each of the plurality of episodes is a specific instance of a medical condition.

The computer-readable storage medium may include instructions that when executed cause processing circuitry to generate a candidate episode pairs list comprising a plurality of candidate episode pairs by performing a Cartesian merge of the plurality of episodes and comparing each of the candidate episode pairs with association information defining related medical conditions. In some embodiments, each of the candidate episode pairs having a particular association level and each of the candidate episode pairs define a parent-child relationship and each of the particular association levels define a relative strength between episodes in each of the candidate episode pairs.

The computer-readable storage medium may include instructions that when executed cause processing circuitry to generate a transition list comprising episode pairs from candidate episode pairs in the candidate episode pairs list and determine attribute relationships between the plurality of episodes for the patient based on the episode pairs in the transition list, the attribute relationships used to attribute items between the plurality of episodes.

Embodiments may also include a computer-implemented method, including identifying, by processing circuitry, episode information for a patient, the episode information comprising a plurality of episodes associated with the patient, each of the plurality of episodes is a specific instance of a medical condition.

The computer-implemented method also including generating, by the processing circuitry, a candidate episode pairs list comprising a plurality of candidate episode pairs by performing a Cartesian merge of the plurality of episodes and comparing each of the candidate episode pairs with association information defining related medical conditions. In some instances, each of the candidate episode pairs having an association level and each of the candidate episode pairs define a parent-child relationship and each of the association levels define a relative strength between episodes in each of the candidate episode pairs;

The computer-implemented method may also include generating, by the processing circuitry, a transition list comprising one or more episode pairs from the candidate episode pairs in the candidate episode pairs list and determining, by the processing circuitry, attribute relationships between the plurality of episodes for the patient based on the episode pairs in the transition list, the attribute relationships used to attribute items between the plurality of episodes.

BRIEF DESCRIPTION OF THE DRAWINGS

Embodiments of this disclosure are illustrated by way of example and not by way of limitation, in the figures of the accompanying drawings in which like reference numerals refer to similar elements.

FIG. 5 illustrates an example of a logic flow to determine attribute relationships.

FIG. 6 illustrates an example embodiment of a table having association information.

FIG. 7 illustrates an example embodiment of a table having episode information.

FIGS. 11A-11D illustrate an example embodiment of a processing flow to generate a transition list from a candidate episode pairs list.

FIGS. 12A-12F illustrate an example of a process to generate attribute relationships using a leveling operation.

DETAILED DESCRIPTION

Figure 1A:
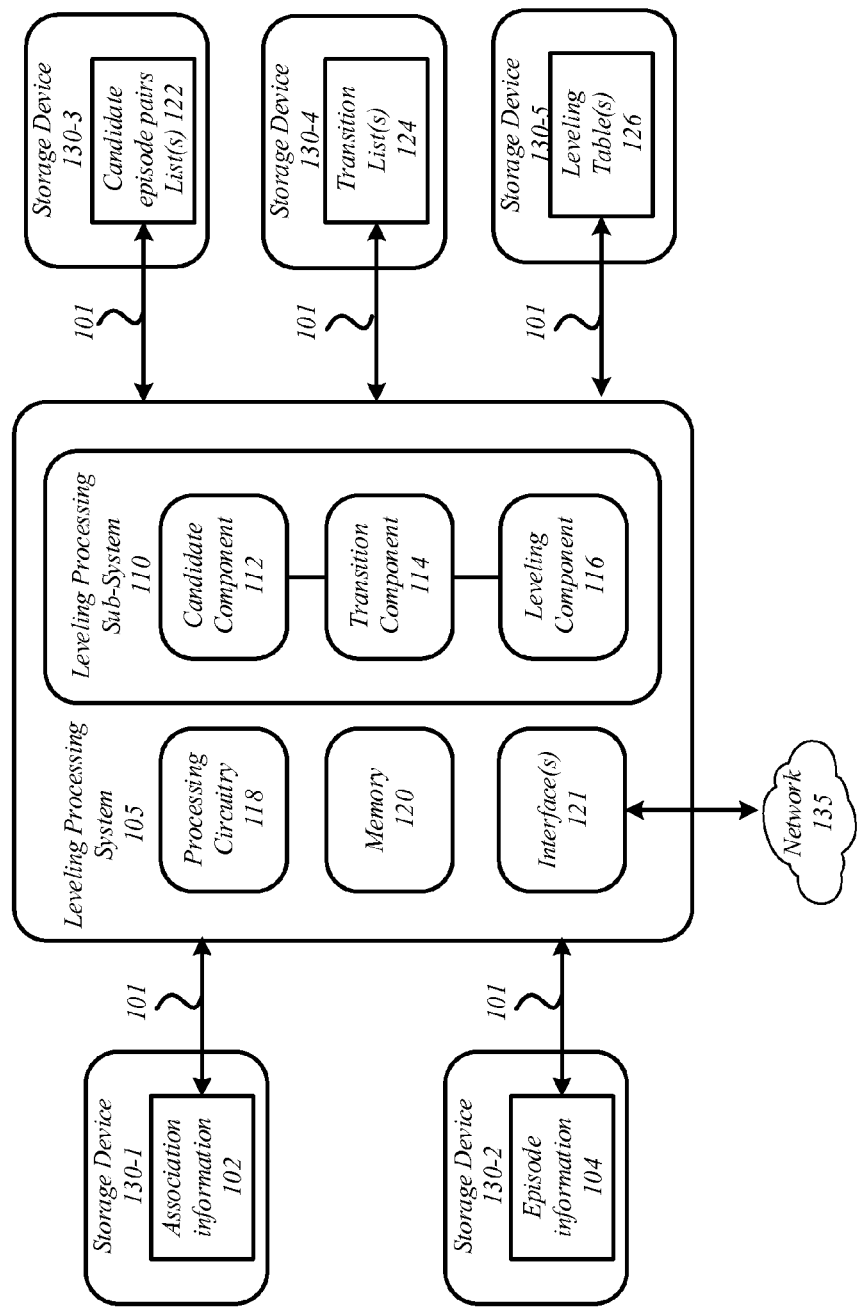
FIG. 1A illustrates an example embodiment of a system to determine attribute relationships between episodes.

With general reference to notations and nomenclature used herein, the detailed description that follows may be presented in terms of program procedures executed on a computer or network of computers. These procedural descriptions and representations are used by those skilled in the art to most effectively convey the substance of their work to others skilled in the art.

A procedure or routine is referred to here and is generally conceived to be a self-consistent sequence of operations leading to a desired result. These operations are those requiring physical manipulations of physical quantities. Usually, though not necessarily, these quantities take the form of electrical, magnetic or optical transmissions capable of being stored, transferred, combined, compared and otherwise manipulated. It proves convenient at times, principally for reasons of common usage, to refer to these transmissions as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations or routines described herein that form part of one or more embodiments. Rather, the operations are machine operations. Useful machines for performing operations of various embodiments include general-purpose digital computers or similar devices.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., Event Stream Processing (ESP)) analytics. Some of these devices may be referred to as edge devices, and may involve edge computing circuitry and/or personal body sensors (e.g., wearables) and/or health-related devices, which can include the medical data described herein.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply queries to the data as it is received and determines which entities receive the processed data.

In other embodiments, network devices may provide a large amount of data, either all at once or streaming over a period of time (e.g., using event stream processing (ESP)). For example, network devices may include local area network devices, such as routers, hubs, switches, or other computer networking devices. These devices may provide a variety of stored or generated data, such as network data or data specific to the network devices themselves. Data may be collected using a variety of sources as communicated via different kinds of networks or locally, such as on a real-time streaming basis. For example, network devices may receive data periodically from network device sensors as the sensors continuously sense, monitor and track changes, such as, for example, the medical data described herein. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations, such as important medical data for multiple patients and medical providers. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined Newly active is determined when the computing device is switched from a standby status to an active status. When the second status is newly active, a last published event block object identifier that uniquely identifies a last published event block object is determined A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Embodiments may also include solving problems associated with processing "big data," e.g. large data sets under which traditional processing techniques are not adequate. More specifically, traditional processing techniques may not process the information in a timely manner that is useful to an end user. In one example, a system may include a leveling processing system coupled with a number of storage devices storing medical information which may consist of thousands or millions of records for patients. The leveling processing system may receive or retrieve this information over one or more communication links for processing. More specifically, the leveling processing system can process this large amount of information by sorting the information for each patient and performing a Cartesian merge to generate candidate lists of episodes or medical events for the patient. The candidate list are processed by the leveling processing system to generate a transition list for each patient. The transition list includes episode pairs that are associated with each other having a parent/child relationship. The episode pairs in the transition list may be used by the leveling processing system to generate a leveling table which includes information indicating a strength of relationship between episodes. Further and as will become apparent in the following description, the information in the leveling table may be used to attribute items, such as cost, between episodes of the episode pairs. By processing the information in this manner, the leveling processing system saves processing cycles which may be used to process other information. Further, a significant amount of time may be saved by the leveling processing system making processing the large amount of information in real-time possible.

FIG. 1A illustrates a general overview of a system 100 for processing information and determining attribute relationships between episodes of medical conditions for patients. The attribute relationships between episodes of medical conditions for a patient may be used to attribute items, such as costs, complications, pharmaceutical prescriptions, and so forth, between the episodes. FIG. 1 illustrates the system 100 including a level processing system 105 coupled with a number of storage devices 130-1 through 130-5 via one or more communication links 101 to determine the attribute relationships. The level processing system 105 may including circuitry, memory, interfaces and a number of components to process information, such as association information 102 and episode information 104. The leveling processing system 105 may generate information including candidate episode pairs list(s) 122, transition list(s) 124 and leveling table(s) 126, which can include attribute relationships between episodes and information to attribute items among the episodes for a patient.

In embodiments, the leveling processing system 105 may include processing circuitry 118 which may include one or more of any type of computational element, such as but not limited to, a microprocessor, a processor, central processing unit, digital signal processing unit, dual core processor, mobile device processor, desktop processor, single core processor, a system-on-chip (SoC) device, complex instruction set computing (CISC) microprocessor, a reduced instruction set (RISC) microprocessor, a very long instruction word (VLIW) microprocessor, or any other type of processing circuitry, processor or processing circuit on a single chip or integrated circuit. The processing circuitry 118 may be connected to and communicate with the other elements of the leveling processing system 105 including the memory 120, interfaces 121 and the leveling processing sub-system 110.

The leveling processing system 105 also includes memory 120 that can be implemented using any machine-readable or computer-readable media capable of storing data, including both volatile and non-volatile memory. In some embodiments, the machine-readable or computer-readable medium may include a non-transitory medium. The embodiments are not limited in this context. The memory 120 can store data momentarily, temporarily, or permanently. The memory 120 stores instructions and data for system 100. The memory 120 may also store temporary variables or other intermediate information while the processing circuitry 118 is executing instructions. The memory 120 is not limited to storing the above discussed data; the memory 120 may store any type of data.

The leveling processing system 105 may also include one or more interfaces 121 which may enable the system to communicate over a network environment 135. In some embodiments, the interfaces 121 can be a network interface, a universal serial bus interface (USB), a Firewire interface, a Small Computer System Interface (SCSI), a parallel port interface, a serial port interface, or any other device to enable the leveling processing system 105 to exchange information.

In embodiments, the leveling processing system 105 can include a leveling processing sub-system 110 having a number of components to process the association information 102 and episode information 104, for example. More specifically, the leveling processing sub-system 110 includes a candidate component 112, a transition component 114 and a leveling component 116.

The leveling processing sub-system 110 can process the association information and episode information, generate a candidate episode pairs list, generate a transition list, and determine attribute relationships or associations between episodes. In some embodiments, the leveling processing sub-system 110 may perform these functions for each of a plurality of patients. For example, each patient may have a candidate episode pairs list, a transition list, and attribute relationships determined or generated such that attribute items may be attributed between episodes for a patient. In some instances, a patient may have more than one candidate episode pairs list, transition list, and determined attribute relationships. Embodiments are not limited in this manner.

In embodiments, the candidate component 112 may receive or retrieve episode information 104 for a patient from a storage device, such as storage device 130-2, via one or more communication links. The candidate component 112 can also receive or retrieve association information 102 from a storage device 130-1. The candidate component 112 can generate a candidate episode pairs list 122, which includes a plurality of candidate episode pairs, by performing a Cartesian merge of the plurality of episodes from the episode information 104 and comparing each of the candidate episode pairs with association information 102 defining related medical conditions. The candidate component 112 may communicate the candidate episode pairs list 122 to a storage device 130-3 for storage and later use, for example.

The leveling processing sub-system 110 can also include a transition component 114 that can, among other things, generate a transition list 124 comprising an episode pair from the candidate episode pairs of the candidate episode pairs list 122. The transition component 114 may generate the transition list 124 using candidate episode pairs from the candidate episode pairs list 122 and identity candidate episode pairs. The transition component 114 can iteratively add candidate episode pairs to the transition list 124 starting with candidate episode pairs with a lowest association level. In some embodiments, the transition component 114 may remove each remaining candidate episode pair from the candidate episode pairs list 122 having a child episode that is a child episode of a candidate episode pair in the transition list 124 as a possibility to include in the transition list 124. After each iteration, the transition component 114 can increase to a next lowest association level associated with candidate episode pairs and repeat the adding and removing processing operations until no candidate episode pair remain in the candidate episode pair list 122. The transition list 124 may be stored in a storage device 130-4 and used to generate a leveling table 126.

In some embodiments, the leveling processing sub-system 110 may also include a leveling component 116 to determine attribute or hierarchal (parent/child) relationships between the plurality of episodes for the patient based on one or more episode pair in the transition list 124. The attribute relationships are used to determine hierarchal relationships between the plurality of episodes. In one example, costs of episodes are attributed to other episodes based on the determined attribute relationship between the episodes. The attribute relationships may be defined and presented in a leveling table 126 which can be stored in a storage device 130-5. The leveling table 126 may be generated by adding episode pairs from the transition list 124 starting with the episode pairs with the lowest association level indicating the highest strength of relationship. The leveling component 116 may also add episode pairs to the leveling table 126 based on attribute relationships of other episode pairs from the transition list 124, as will be discussed in more detail below with respect to FIGS. 12A-12F. For example, if an episode is a parent of another episode and the other episode is a parent of a third episode, the episode is also a parent of the third episode at a particular level. These attribute relationships at particular association levels may be determined by the leveling operation. A specific example may include, a knee replacement that is a parent or cause of a first heart attack and the first heart attack is a parent or cause of a second heart attack. Thus, the knee replacement is the parent or cause of the second heart attack at a particular level.

The leveling component 116 may indicate in the leveling table 126 an association level for each episode pair that can be used to attribute items between the episode pair. The association level for each episode pair may also be used to determine a strength of relationship between the episode pair. For example, a lower association level can indicate a stronger relationship than a higher association level, or vice versa.

As mentioned, system 100 can include storage devices 130-1 through 130-5 which may be any type of storage or memory capable of storing information, such as hard disks, memory devices, tape devices, and so forth. In some embodiments, the storage devices 130-1 through 130-5 may be the same storage device. For example, any one or more of storage devices 130-1 through 130-5 may be the same hard drive. However, in the same or different embodiments, the storage devices 130-1 through 130-5 may be different storage devices. In another example, any one or more of storage devices 130-1 through 130-5 may be different hard drives. In some embodiments, the storage devices 130-1 through 130-5 may be local or proximate to the leveling processing system 105. However, the storage devices 130-1 through 130-5 can also be remote or at a different location than leveling processing system 105. In some embodiments, the storage devices 130-1 through 130-5 may each be a database system having a number of hard disks to store information. The storage devices 130-1 through 130-5 may be coupled to the leveling processing system 105 by one or more communication links 101 which may be part of a networking environment 135. Embodiments are not limited in this manner. The storage devices 130-1 through 130-5 may store information, such as the association information 102 and episode information 104. In embodiments, the association information 102 and episode information 104 may be stored in a data structure such as a list, a file, a table, a spreadsheet, a document, and so forth. In some embodiments, the association information 102 and/or episode information 104 may be stored locally or may be provided by a remote facility or device.

In embodiments, the association information 102 represents clinical knowledge regarding relationships that exist between medical conditions. For example, the association information 102 may define a parent and child relationship between medical conditions. In other words, a parent medical condition may be a contributory factor or cause of a child medical condition. The association information 102 may define the parent/child relationships between episodes at different association levels based on a relative strength between the conditions or a likelihood of one episode causing another episode. For example, a lower association level may indicate a stronger relationship between episodes of an episode pair than a higher association level. The association level may also be a relative strength between episode pairs. For example an episode pair having an association level with lower level has a stronger relationship than an episode pair having a higher level. Embodiments are not limited in this manner and in some embodiments a higher association level may indicate a stronger relationship.

The episode information 104 includes a plurality of episodes where each episode is a specific instance of a medical condition. The episode information 104 may include episodes for a plurality of patients and each episode may be associated with one of the patients. For example, a patient may be associated with one or more episodes, such as a heart attack, a stroke and a knee replacement operation and so forth, which may have occurred to the patient. The association information 102 and the episode information 104 may be used by the leveling processing system 105 to determine the attribute relationships of episodes for a patient at particular association levels such that items or costs of an episode may be attributed to one or more other episodes.

In embodiments, the leveling processing system 105 may receive and/or retrieve the association information 102 and the episode information 104 from the storage devices 130-1 and 130-2, respectively, via a communication link 101. The association information 102 and episode information 104 may each be a large data set and may be considered "big data" under which traditional processing techniques are not adequate. More specifically, the traditional processing techniques may not process the information in a timely manner that is useful to an end user. Thus, embodiments are generally directed to processing the association information 102 and episode information 104 using the level processing system 105 in an efficient manner to lower processing times and provide information to an end user for use in attributing items between medical episodes. These benefits and other details will become more apparent in the following description.

Figure 1B:
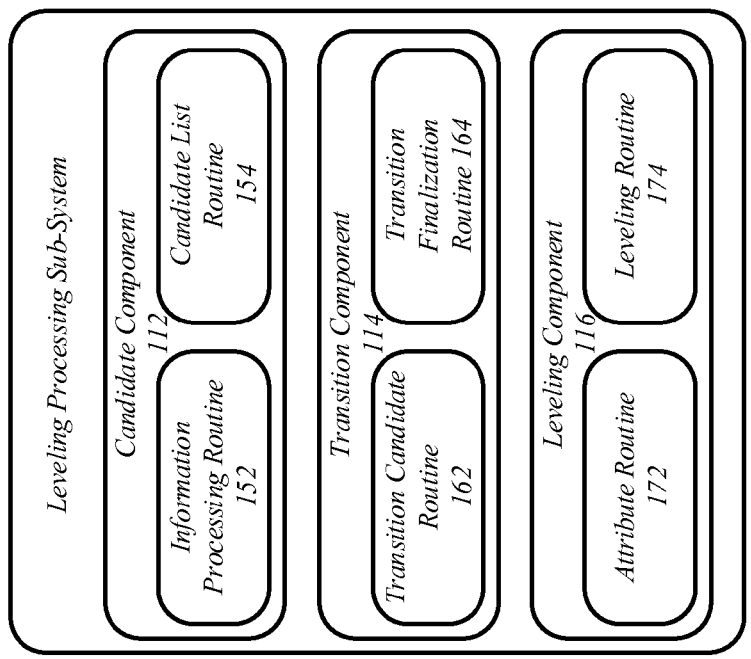
FIG. 1B illustrates an example embodiment of a leveling processing sub-system to process information.

FIG. 1B illustrates an example embodiment of a leveling processing sub-system 110 that may be part of a leveling processing system 105 to process information, generate a candidate episode pairs list, generate a transition list, and determine attribute relationships or associations between episodes. In some embodiments, each of the components may include a number of routines to perform various functions and processing.

Figure 2A:
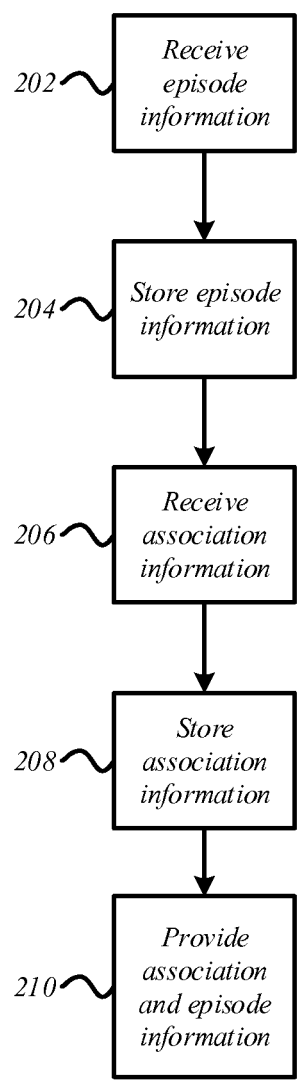
FIG. 2A illustrates an example of a logic flow to process episode and association information.

In embodiments, the candidate component 112 includes an information processing routine 152 and a candidate list routine 154. The information processing routine 152 can receive, retrieve, and identity information that may be used by the leveling processing sub-system 110 to perform various processing and functions. FIG. 2A illustrates one possible logic flow 200 that may occur during operation of the information processing routine 152 of the candidate component 112. Thus, reference is now made to FIG. 2A. At block 202, the information processing routine 152 may receive, retrieve, and/or identity episode information. As previously mentioned, the episode information may include one or more episodes, such as one or more specific instances of a medical condition associated with a patient. In embodiments, the information processing routine 152 may receive or retrieve the episode information from a remote or local system, device, or computer. In some instances, the episode information may be communicated to the leveling processing sub-system 110 in a data structure in a compatible format for processing.

At block 204, the information processing routine 152 can store the episode information in storage or memory, such as one or more of the storage devices 130-1 through 130-5 or memory 120. The information processing routine 152 may retrieve, receive, and/or identity association information at block 206. The association information includes information defining related medical conditions or episodes. In some instances, the association information may define related episodes as a condition and sub-condition where the condition may cause the sub-condition. In other words, the condition is a parent of a child sub-condition. The association information may also define an association level for each related episode pair. The association level indicates the strength of the relationship between the condition (parent) and sub-condition (child). In some instances, a lower association level may indicate a stronger relationship and a higher association level may indicate a relative weaker relationship between episodes. Embodiments are not limited in this manner. At block 208, the information processing routine 152 may store the association information in storage or memory, such as one or more of the storage devices 130-1 through 130-5 and memory 120.

In some embodiments, the information process routine 152 may provide the association information and episode information to other components and routines of the leveling processing sub-system 110 at block 210. The information process routine 152 can communicate the association information episode information to the other components and routines and/or make the information available for retrieval. In some embodiments, the information processing routine 152 may put the information into a format that may be used by the other components and routines.

Although FIG. 2A illustrates certain blocks occurring in a particular order, various embodiments are not limited in this manner. For example, one or more blocks may occur in parallel or simultaneously. In another example, one or more blocks may occur before or after other blocks and may be in a different order. In addition, the blocks are not dependent upon one another.

Figure 2B:
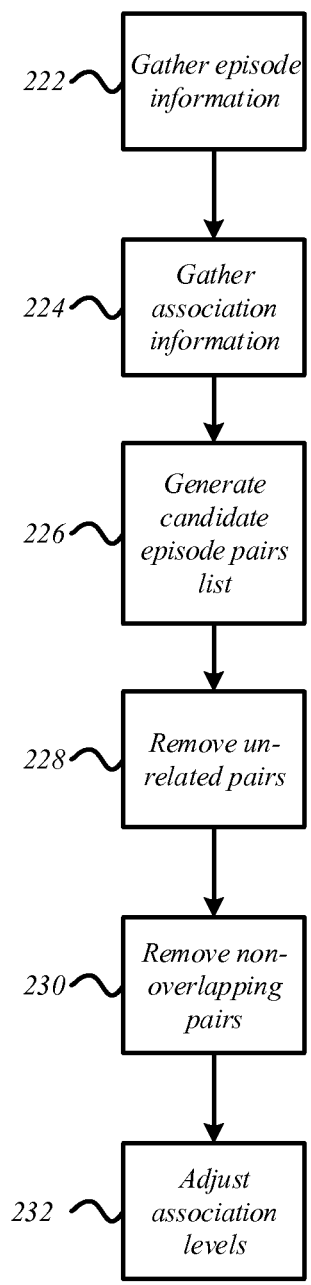
FIG. 2B illustrates an example of a logic flow to process candidate episode pairs list.

In some embodiments, the candidate component 112 may also include a candidate list routine 154 which may generate a candidate episode pairs list. FIG. 2B illustrates one possible logic flow 220 for generating a candidate episode pairs list for a patient using association information and episode information by the candidate component 112. Reference is now may to FIG. 2B. At blocks 222 and 224, the candidate list routine 154 may gather episode information and association information. The candidate list routine 154 may receive or retrieve the information from the information processing routine 152 and/or from one or more storage devices. The episode information and association information may be gathered in a format suitable for processing by the candidate list routine 154.

In embodiments, the candidate list routine 154 generates an initial candidate episode pairs list which includes a plurality of candidate episode pairs at block 226. The candidate episode pairs list may be generated for a patient by using the episodes in the episode information and performing a Cartesian merge of the episodes. The candidate list routine 154 also compares each of the candidate episode pairs generated by the Cartesian merge with association information to determine if a relationship exists between the episodes. Candidate episode pairs not listed as having an association or relationship in the association information may be removed as a possible candidate episode pairs from the candidate episode pairs list at block 228.

The logic flow 220 includes removing non-overlapping candidate episode pairs from the candidate episode pairs list at block 230. More specifically, a determination may be made as to whether episodes of a candidate episode pair overlap in time, and based on the determination, the candidate list routine 154 removes candidate episode pairs that do not include episodes that overlap in time from the candidate episode pairs list. Overlap criteria may be defined for episode pairs which may include an overlap or a trigger time period in which a child episode must start within to be considered as having a relationship with a parent episode. The overlap time period may include a start time or day and end time or day. In one example, for episodes of candidate episode pairs to be considered overlapping in time the child episode must start on or after the start day, but before or on the end day of a parent episode. Note that the child episode may end after the end day of the parent episode for the overlap time period. The overlap time period may be the start day of the parent episode, but is not required to be. For example, the start day of the overlap time period may be offset from the start day of a parent episode. The overlap time period can be defined in the association information and may be a defined amount of time in which complications of an episode trigger or cause another episode.

In some embodiments, the candidate list routine 154 may adjust an association level for candidate episode pairs in the candidate episode pairs list by performing a stacking operation or an offset operation at block 232. More specifically, the association level for each candidate episode pair having a parent episode that is a child episode in another candidate episode pair at the same association level may be adjusted. To perform the adjustment using the offset operation a determination is made as to whether a candidate episode pair meeting the criteria includes an offset adjustment value in the association information. If an offset adjustment value exists, the candidate list routine 154 subtracts the offset adjustment value from the association level of the candidate episode pair of the parent episode to generate a new association level. By way of example, if a knee replacement episode is a parent to a heart attack episode and that heart attack episode is a parent to a stroke episode at the same association level, the heart attack/stroke episode pair may have an adjusted association level based on an offset adjustment value, e.g. one less than its current association level.

In some embodiments, a stacking operation may be performed to adjust the association level for candidate episode pair having a parent episode that is a child episode in another candidate episode pair. During a stacking operation, the candidate list routine 154 does not require the use of the offset adjustment value in the association information to perform the operation. The stacking operation uses the candidate episode pairs list and each candidate episode pair at a particular association level is evaluated to determine if a parent episode in a candidate episode pair is a child episode of another candidate episode pair at the same association level and identifies the other candidate episode pair having the parent episode as being 'stacked'. Each episode of each candidate episode pair is compared to all of the other episodes in the candidate episode pairs list at the same association level. Each episode identified as being stacked increments its association level by a decimal value, such as 0.1, 0.01, 0.001, etc., depending on need. Thus, if the association level for a candidate episode pair is 3, the new association level for stacked candidate episode pair may become 3.1, for example.

Further, the process of increasing the candidate episode pairs' association levels that are 'stacked' by a decimal value is repeated within a set of identified stacked candidate episode pairs. That is to say, each set of candidate episode pair with the same adjusted association levels need to be evaluated. For example, all candidate episode pairs having an adjusted association level of 3.1 need to be evaluated to determine if a parent episode in a candidate episode pair is a child episode of another candidate episode pair at the same association level, e.g. 3.1. The association level for these 'stacked' candidate episode pairs is increased again by a decimal value. In this example, the association value for the 'stacked' candidate episode pairs may increase to 3.2. The above-discussed process is repeated for every candidate episode pair at every association level and new association level until all of the candidate episode pairs are evaluated.

Once the candidate episode pairs may be finalized or considered a final candidate episode pairs once episode pairs been evaluated against the association information, determined to have a child episode during a trigger time period, and evaluated for association level adjustments. The final candidate episode pairs list may be used to generate a transition list and a leveling table.

Figure 3A:
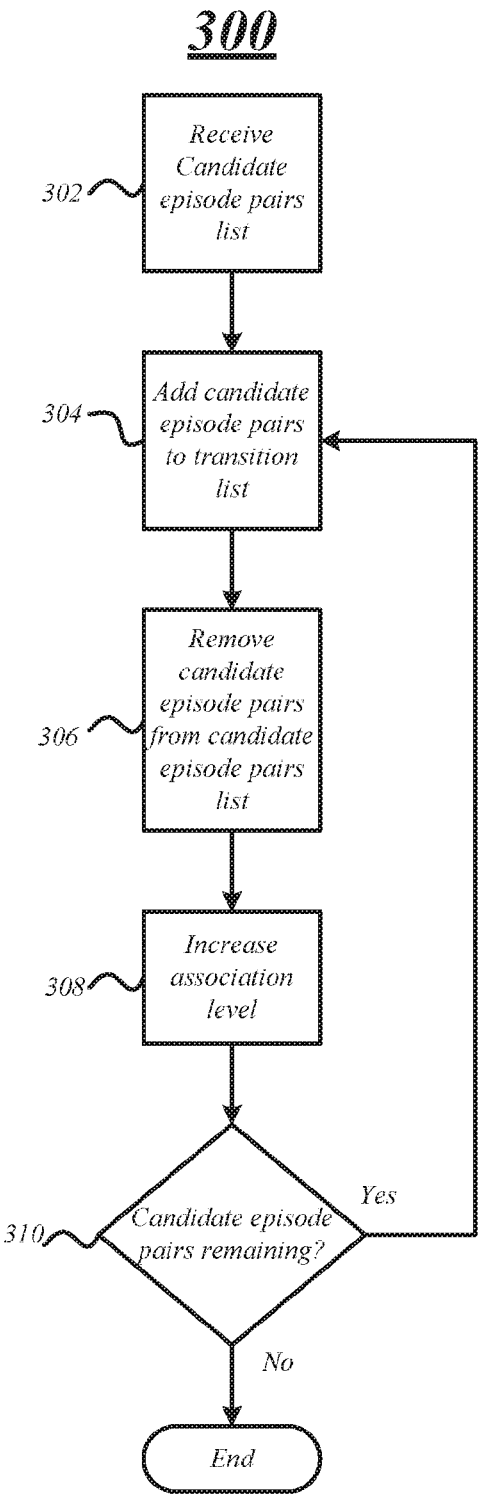
FIG. 3A illustrates an example of a logic flow to process a transition list.

As previously mentioned, the leveling processing subsystem 110 may include a transition component 114 that may have one or more routines to process information to generate a transition list. The one or more routines may include a transition candidate routine 162 and a transition identity routine 164. The transition candidate routine 162 may generate the transition list using a candidate episode pairs list and the transition identity routine 164 may add identity episode pairs to the transition list to be used during the creation of the leveling table. FIG. 3A illustrates one possible logic flow 300 for generating a transition list based on the candidate episode pairs list via transition component 114. Reference is now may to FIG. 3A.

At block 302, the transition candidate routine 162 receives a candidate episode pairs list including candidate episode pairs. The candidate episode pairs list may be a finalized candidate episode pairs list, as previously discussed above. At block 304, the transition candidate routine 162 will add candidate episode pairs from the candidate episode pairs list to the transition list starting with the lowest association level and increasing in association level after each iteration of blocks 304-310. The candidate episode pairs at the same association level may be added to the transition list and each remaining candidate episode pairs from the candidate episode pairs list having a child episode that is a child episode of an episode pair in the transition list is removed from the candidate episode pairs list at block 306. Thus, the removed candidate episode pairs will not be added to the transition list. At block 308, the association level at which candidate episode pairs are added is increased to the next lowest association level. For example, if the candidate episode pairs added at block 304 have an association level of two (2), the association level is increased to three (3) for evaluation. At block 310 a determination is made as to whether any candidate episode pairs remain in the candidate episode pairs list to be added to the transition list. If at block 310 additional candidate pairs remain, blocks 304-310 may be repeated in an iterative fashion until no candidate episode pair remain to be added to the transition list and the logic flow ends. The generated transition list may include episode pairs from the candidate episode pairs in an order starting with the lowest association level going to the highest association level. The transition list may be used to generate the level table as discussed later in this Specification.

In some instances, it is possible to have a reciprocal relationship for candidate episode pairs in the candidate episode pairs list to be added to the transition list at block 304. For example, a first episode may be a parent to a second episode in a first candidate episode pair and at the same association level the second episode may be a parent to the first episode in a second candidate episode pair. In this case, the correct parent/child relationship and the candidate episode pair added to the transition list at block 304 may be determined by tiebreaker criteria. In one example, the claim or episode type may be used as the tiebreaker criteria. One tiebreaker criteria may be the type of episode. For example, an in-patient procedure may beat an out-patient procedure which may beat a professional or office visit. In another example, the absolute date on which the episode occurred may be used. In this example, the episode which occurred first may be considered the parent episode. In a third example, if the episodes are both medical conditions associated with birthing, such as vaginal delivery vs. caesarian section, the vaginal delivery may be considered as the parent episode. Embodiments are not limited to these tiebreaker criteria.

Figure 3B:
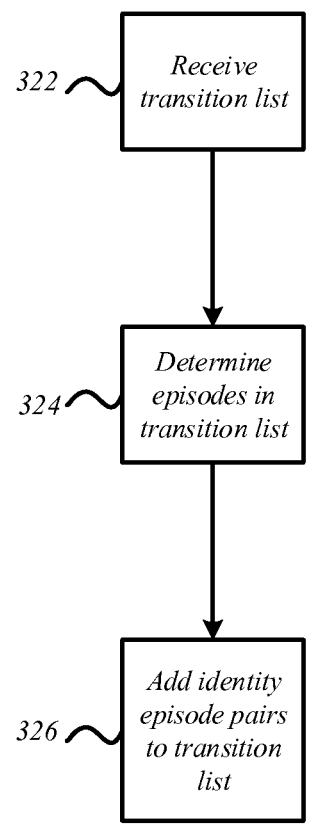
FIG. 3B illustrates an example of a logic flow to process identity episode pairs.

In some embodiments, the transition component 114 may include a transition identity routine 164 to add identity episode pairs for each episode in the transition list. FIG. 3B illustrates an example logic flow 320 to add identity episode pairs by the transition component 114. At block 322, the transition identity routine 164 may receive the transition list having episode pairs. The episode pairs may include all the candidate episode pairs added to the transition list as previously discussed above with respect to FIG. 3A. In some embodiments, the transition identity routine 164 may receive the transition list from the transition candidate routine 162, for example. In some instances, the transition identity routine 164 may retrieve or receive the transition list from a storage device. Embodiments are not limited in this manner.

At block 324, the transition identity routine 164 may determine each episode that is listed in the transition list. For example, the transition identity routine 164 may analyze each episode pair and identify each episode. The transition identity routine 164 may add an identity episode pair for each identified episode to the transition list at block 326. If an episode is in the transition list more than once, e.g. as a parent and a child, the transition identity routine 164 will only add one instance of the identity episode pair for the episode to the transition list. In some instances, the transition identity routine 164 may add the identity episode pairs to the transition with a lowest association level. For example, all of the identity episode pairs may have an association level of one (1). However, embodiments are not limited to this example. Any association level may be used as long as it is the lowest association level compared to the episode pairs previously in the transition list.

Figure 4A:
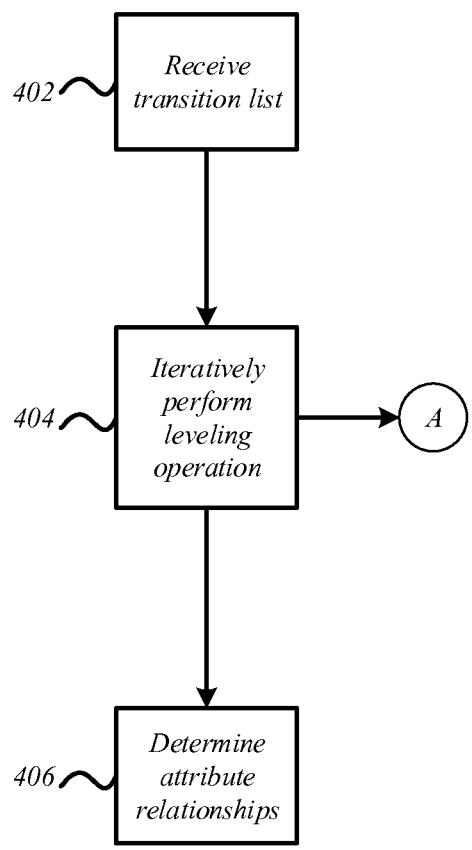
FIG. 4A/4B illustrate an example of a logic flow to process a leveling operation.

The leveling processing sub-system 110 also includes a leveling component 116 that may have one or more routines to generate a leveling table to determine attribute relationships. The one or more routines may include an attribute routine 172 and a leveling routine 174. The attribute routine 172 may determine attribute relationships between episodes based on a leveling table and the leveling routine 174 may generate the leveling table. FIG. 4A illustrates one possible logic flow 400 for processing a transition list to determine attribute relationships between episodes by the leveling component 116. Reference is now may to FIG. 4A.

Figure 4B:
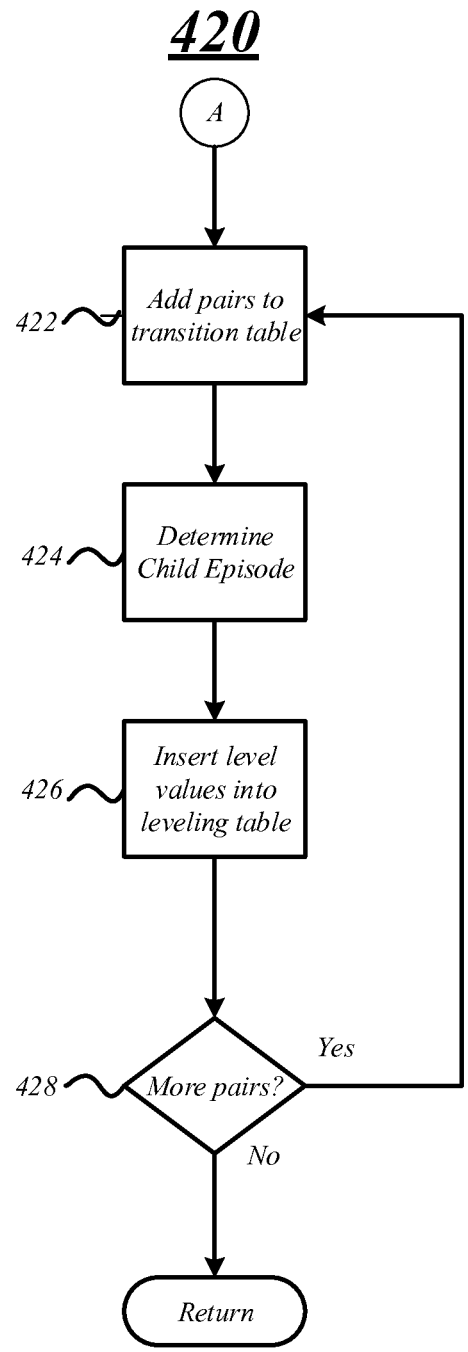

At block 402, the attribute routine 172 may receive or retrieve a transition list for use in generating a leveling table. In some embodiments, the transition list may be received from the transition identity routine 164 and/or one or more storage devices. The attribute routine 172 may iteratively perform a leveling operation by invoking the leveling routine 174 at block 404. One possible logic flow for the leveling routine 174 is illustrated by logic flow 420 of FIG. 4B operable by the leveling component 116. Thus, reference is now made to FIG. 4B.

In embodiments, the leveling routine 174 may add one or more episode pair from the transition list to the leveling table at block 422. The episode pairs in the transition list having the lowest association level are first added to the leveling table. During the initial iteration, the identity episode pairs may be first added to the leveling table. After the initial iteration, each episode pair may be added to the leveling table one or more times based on a number of times the child episode of the episode pair being added is also a child episode of an episode pair already in the leveling table. More specifically, an episode pair from the transition list is added to the leveling table after each episode pair in the leveling table where the child episode of the to be added episode pair is also a child episode of an episode pair already added to the leveling table.

At block 424, the leveling routine 174 may determine a new child episode for each newly added child episode using the child episode directly above the newly added child episode in the table when the child episode of the newly added episode pair is a parent episode of an episode pair previously added to the table. In other words, a new child episode is replaced with a previously inserted child episode. By way of example, if a first heart attack is a parent of a second heart attack at an association level of two (2), and a knee replacement is a parent of the first heart attack at an association level of three (3). The knee replacement becomes the parent episode of the second heart attack at the association level of three (3).

The leveling routine 174 may insert level values into the leveling table for each newly added episode pair at block 426. The level values may be added to the leveling table at the association level for the episode pair and may be a whole number or a fraction. For example, if a child episode is in a single episode pair at a particular association level the level value maybe one (1). However, if the child episode is a child episode in a number of episode pairs the level value may be a weighted level value. The level value may be the inverse of the number of times the child episode is in the episode pairs at a particular association level. For example if a child episode appears twice in episode pairs at a particular association level the level value may be ½ or 0.5. Embodiments are not limited in this manner and other level values may be contemplated.

At decision block 428, the leveling routine 174 may determine whether more episode pairs exist in the transition list at decision block 428. Blocks 422 through 428 may be repeated until all of the episode pairs in the transition list are processed. The logic flow 420 may end or return to logic 400 once the episode pairs are processed.

Returning back to logic flow 400, the attribute routine 172 may determine attribute relationships at block 406. The leveling table generated at block 404 and the leveling routine 174 may be used to determine attribute relationships at particular association levels. More specifically and as will be discussed in more detail below, the level values in the leveling table may be used to determine attribute relationships at particular association levels. For example, costs of a child episode may be attributed to the costs of a parent episode at a particular association level when the episode pairs (parent/child) has a level value greater than zero (0) at the particular association level. In some instances, a level value of one (1) at the particular indicates that the entire cost of the child episode may be attributed to the parent episode. If the level value is a fractional value then a portion of the cost of the child episode may be attributed to the parent episode. These and other details will become more apparent when discussing FIGS. 6-12F.

FIG. 5 illustrates an example embodiment of logic flow 500 to process episode information and association information. The logic flow 500 may be representative of some or all of the operations executed by one or more embodiments described herein. For example, the logic flow 500 may illustrate operations performed by the systems, devices, logic flows and so forth discussed in FIGS. 1-4B and 6-13.

In the illustrated embodiment shown in FIG. 5, the logic flow 500 may include identifying episode information for a patient, the episode information comprising a plurality of episodes associated with the patient, each of the plurality of episodes is a specific instance of a medical condition at block 505. As previously mentioned, the episode information may be made available and/or provided to a level processing system such that it may use the episode information to determine attribute relationships between each of the episodes. As illustrated in FIG. 7, the episode information may be in an episode information table 700 and includes episode identification information 702, patient identification information 704, medical condition information 706, episode classification information 708, an episode start date 710, an episode trigger date 712, episode day information 714 and an episode end date 716.

The episode identification information 702 is a unique identification for each instance of a medical condition that has occurred to a patient. Further, the episode information may include information for a number of patients and each patient may be uniquely identified by the patient identification information 704. The medical condition information 706 may be an identifier of a specific medical condition. In some instances, the medical condition information 706 may be a name or an abbreviation of a medication condition, for example. Each of the episodes may be identified in a particular classification by the episode classification information 708, e.g. an acute episode, a procedural episode, or a chronic episode. The episode classification information 708 is based on the how the episode starts and ends. For example, an acute episode is generally sudden with little or no prior action and typically have a finite duration. A procedural episode is generally planned with prior action taken to prepare for the care and has a finite duration, for example. A chronic episode may start suddenly or gradually, but generally does not have a finite duration.

In some embodiments, each of the episodes may be associated with a number of dates and date information. For example, each episode may have an episode start date 710 which may be the actual date on which the episode took place. In addition, each episode can include an episode trigger date 712 which can be the date the episode occurred or may be a different date. For example, the episode trigger date 712 may be a date prior to the episode start date 710 and correspond with a date on which an event or conditioned triggered the episode. The episode information may also include episode day information 714 which may be a number of days over which the episode has taken place. The episode information can also include an episode end date 716 which is the date on which the episode ended. Although, FIG. 7 illustrates the episode information in a table format, embodiments are not limited in this manner and the episode information may be provided and identified in any format suitable for processing by the leveling processing system.

Returning to FIG. 5, the logic flow 500 includes generating a candidate episode pairs list comprising a plurality of candidate episode pairs by performing a Cartesian merge of the plurality of episodes and comparing each of the candidate episode pair with association information defining related medical conditions, each of the candidate episode pairs having a particular association level and each of the candidate episode pairs define a parent-child relationship, each of the particular association levels define a relative strength between episodes in a candidate episode pair at block 510. The Cartesian merge returns ordered episode pairs of all episodes in the episode information to generate candidate episode pairs in the candidate episode pairs list. At this point, identity candidate episode pairs may be removed from the candidate episode pairs list. In addition, each of the candidate episode pairs is compared against association information to determine whether a relationship is defined and exists between the episodes of the candidate episode pairs. If a relationship does not exist, the candidate episode pair is removed from the candidate episode pairs list. However, if a relationship does exist additional criteria may be evaluated.

The association information may include information for the leveling processing system to determine if a candidate episode pair has a possible relationship. FIG. 6 illustrates a table 600 including association information in a parent/child relationship format. More specifically, FIG. 6 illustrates the association information having an episode parent 602 and an episode child 604. Thus, association information includes known or defined related episodes in a parent/child relationship format. In embodiments, the episode parent 602 and the episode child 604 are each medical conditions and may be identified by name or abbreviation. In addition to identifying the medical conditions by name or abbreviation, the association information also includes episode parent numbers 606 and episode child numbers 608 to identify parent and child episodes by a numerical identifier.

In embodiments, the association information includes an association level 610 for each of the episode pair. The association level 610 may be a numerical value that defines the relative strength of a relationship between episodes of the episode pair compared to other episode pairs. In some instances, the numerical value may be an integer value greater than or equal to 1 and a lower numerical value indicates a stronger relationship compared to other episode pairs that have a higher numerical value. For example an episode pair having an association level 610 of 1 has a stronger relationship than an episode pair having an association level 610 of 2. However, embodiments are not limited in this manner and other values may be used to communicate a strength of relationship between episodes.

The association information can also include a start day 612 and an end day 614. The start day 612 and end day 614 can be values that indicate an augmentation to the standard window for relationship consideration, e.g. an overlap period. For example, a start day 612 may change the beginning of the overlap period and an end day 614 may change the end of the overlap period. Additionally, the association information includes a relationship type 616 to indicate the type of relationship between the episodes. For example, one relationship type may be a complication (C), where a child episode may be a complication arising out of a parent episode. Other types of relationship types may exist, such as a typical relationship. For example, a child episode is a typical part of care of a parent episode. In some embodiments and as previously discussed, the association information can also include an offset value 618 which may be used when a candidate episode pair has a parent episode that is a child episode in a second candidate episode pair. The offset value 618 may be subtracted from the current association level 610 to generate a new association level for the episode pair. This may be done so that the episode in episode pairs at different association levels.

Returning to FIG. 5, logic flow 500 includes generating a transition list comprising episode pairs from the candidate episode pairs list of candidate episode pairs at block 515. The transition list may include episode pairs in an ordered list based on association levels and is derived from the candidate episode pairs in the candidate episode pairs list. Episode pairs having the same association level may be grouped together and in some instances, may be ordered from a lowest association level to a highest association value, or vice versa. Embodiments are not limited in this manner. Moreover, the transition list may include as episode pairs the candidate episode pairs that are determined to have a relationship based on the association information and determined to overlap in time.

At block 520, the logic flow 500 includes determining attribute relationships between the plurality of episodes for the patient based on the episode pairs in the transition list, the attribute relationships can be used to determine attribute relationships between the plurality of episodes. In some embodiments, the attribute relationships can be determined at specific association levels based on defined parent/child relationships in the association information. As previously discussed, each episode of a medical condition has one or more parent episodes depending on which association level is being analyzed. For example, a first heart attack may be a parent of a second heart attack at a first association level. However, a knee replacement may be a parent of the second heart attack at a second association level. This may be the case because the parent of the first heart attack is the knee replacement. Thus, the knee replacement causes the first heart attack which causes the second heart attack. The relationship between the knee replacement and the first heart attack and the relationship between the first heart attack and the second heart attack may be stronger than the relationship between the knee replacement and the second heart attack. This difference in relationship strengths is illustrated by the different association levels for the episode pairs.

Figure 8A:
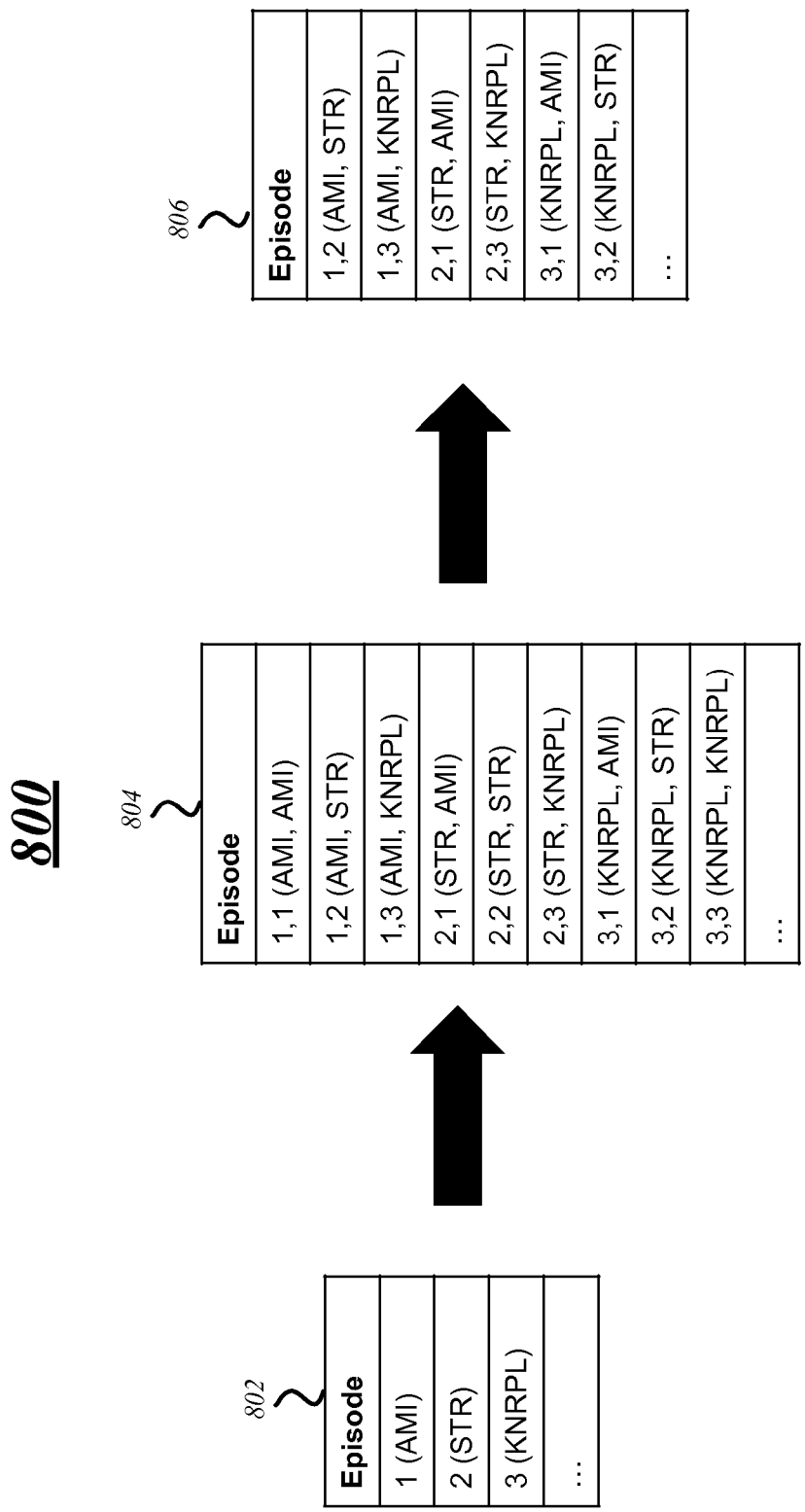
FIGS. 8A/8B illustrate example of process diagrams to generate a candidate episode pairs list.

FIGS. 8A/8B illustrate examples of process diagrams 800 and 850 to generate a candidate episode pairs list. As previously mentioned, the information used to generate and process the candidate episode pairs list includes the episode information and the association information. FIG. 8A illustrates three episodes in list 802 for a patient. The episodes in list 802 may be from episode information. In the illustrated example, the episodes include a heart attack (AMI), a stroke (STR) and a knee replacement (KNRPL). Embodiments are not limited to these examples and the episodes can include any medical condition.

A Cartesian merge may be performed on the episodes in list 802 to generate an initial candidate episode pairs list 804. The Cartesian merge returns ordered episode pairs of all episodes in the episode information to generate the candidate episode pairs in the initial candidate episode pairs list. The initial candidate episode pairs list 804 includes identity candidate episode pairs, for example (1, 1), (2, 2) and (3, 3). These identity candidate episode pairs may be removed from the initial candidate episode pairs list 804 to generate the candidate episode pairs list 806.

Figure 8B:
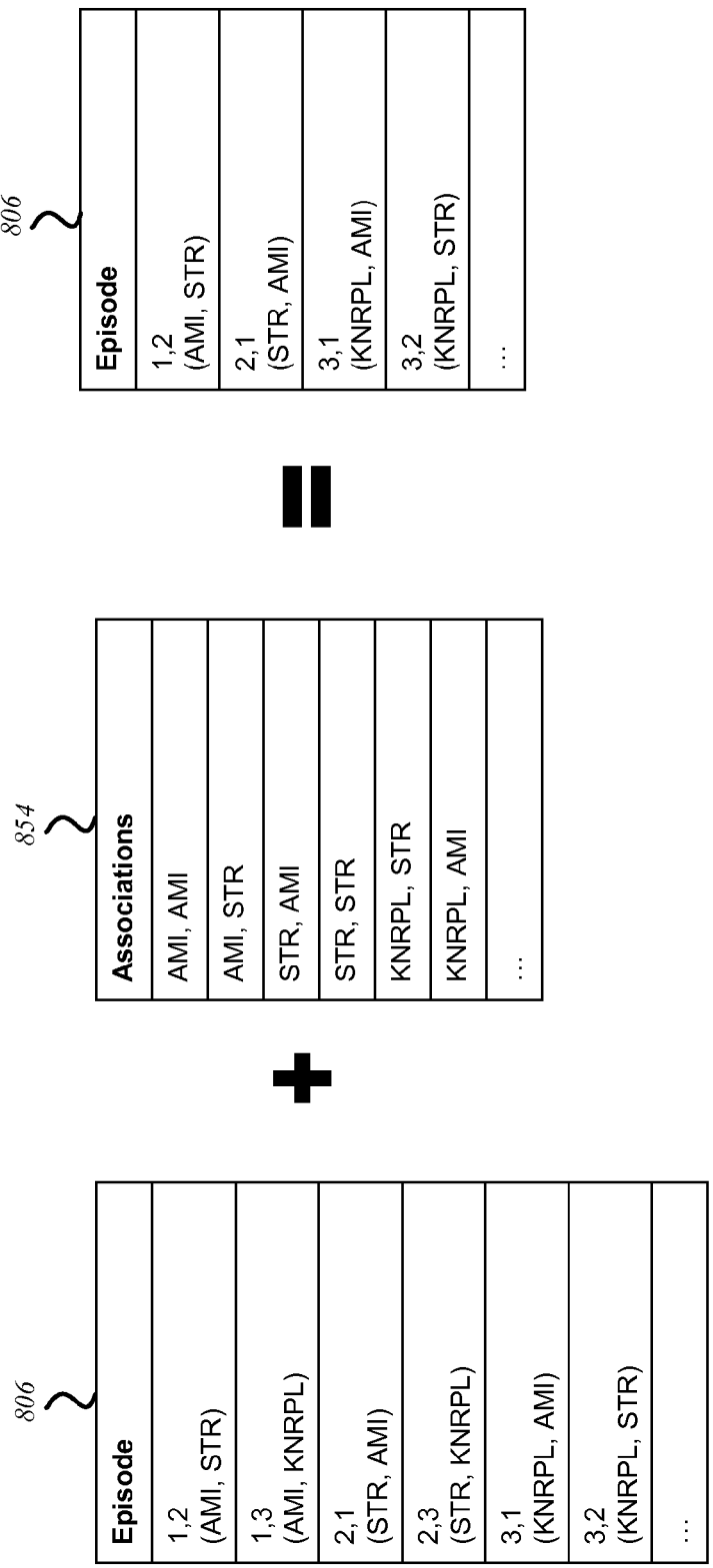

FIG. 8B shows further refinement of the candidate episode pairs list 806 by comparing the candidate episode pairs in the candidate episode pairs list 806 with the association information in list 854. As previously mentioned, the association information defines episodes that have parent/child relationships. Thus, candidate episode pairs not listed in the association information in list 854 may be removed from the candidate episodes pairs list 806. In some instances, the candidate episode pairs list 806 may require further refinement to determine whether the remaining episodes in the candidate episode pairs overlap in time to ensure that a relationship does exist.

Figure 9A:
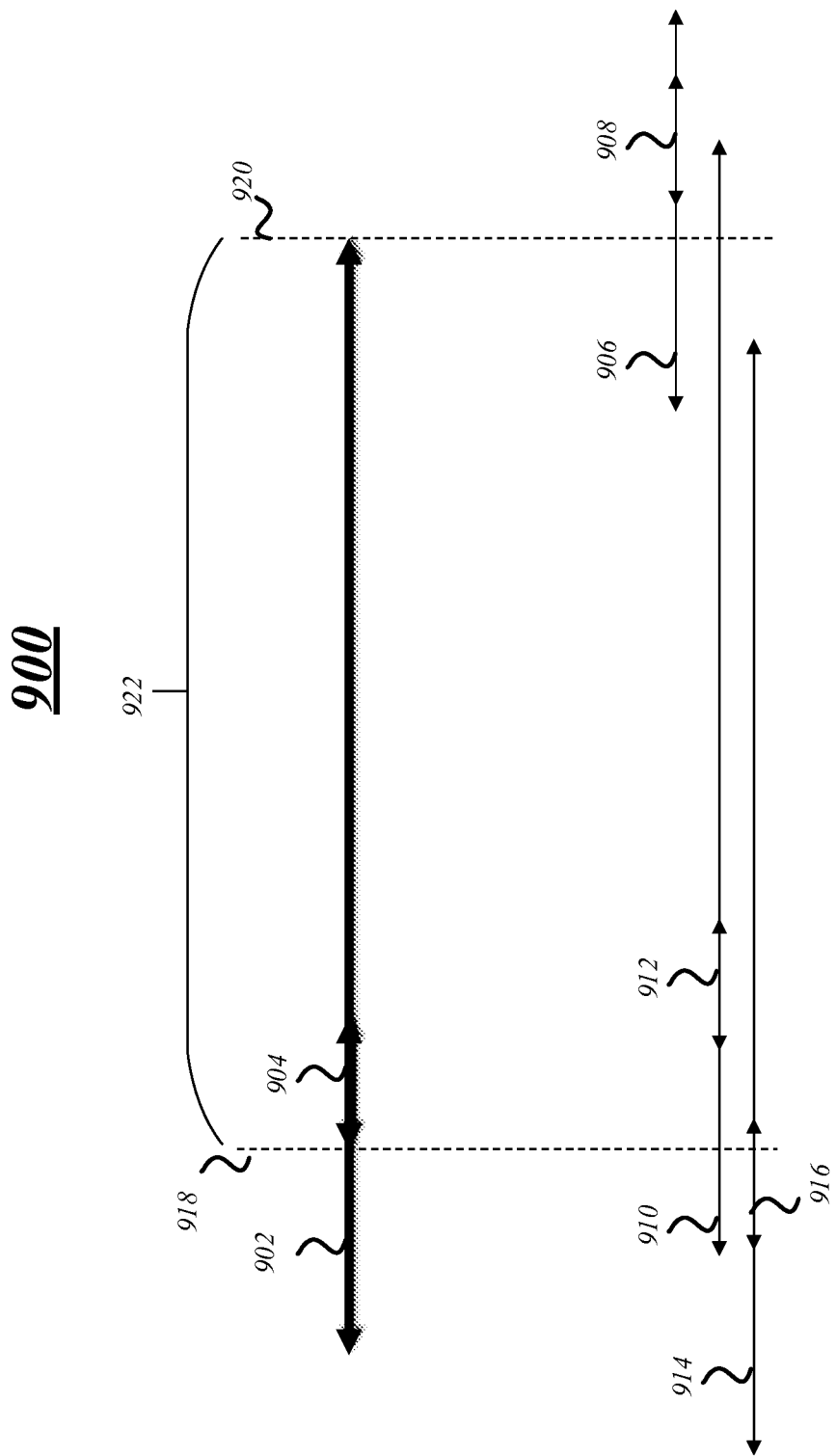
FIGS. 9A/9B illustrate examples of timing diagrams for episode pairs.

FIGS. 9A/9B illustrate example timing diagrams 900 and 950 to determine whether episodes overlap in time to ensure there is a relationship between the episodes. In FIG. 9A, the parent episode timing information is illustrated by episode duration 902 and three potential child episodes are illustrated by episode durations 906, 910 and 914. The occurrences of the episodes or episode trigger periods are illustrated by episode trigger durations 904, 908, 912 and 916. More specifically, FIG. 9A illustrates the parent episode having episode trigger duration 904. Similarly, each potential child episode is illustrated having episode trigger durations. Specifically, a first potential child episode occurrence has an episode trigger duration 908 during duration 906, a second potential child episode occurrence has an episode trigger duration 912 during duration 910 and a third potential child episode occurrence has an episode trigger duration 916 during duration 914.

Further, FIG. 9A illustrates a general overlap period 922 based on overlap criteria having a start day 918 and an end day 920. A general overlap period including the start day and the end day may be defined in the association information. However, in some instances, the general overlap period may be based on general medical knowledge for an episode. For example, if the association information does not include information defining the overlap period including the start day and end day, defined default values based on general medical knowledge may be used. In the illustrated example in FIG. 9A, the overlap period 922, start day 918 and end day 920 are not defined in association information and therefore, default values are used.

For a potential child episode to be considered an actual child episode of the parent episode, the potential child episode must trigger within the overlap period. In FIG. 9A, the first potential child episode triggers (start of episode trigger duration 908) after the end day 920 and therefore cannot be a child of the parent episode. The second potential child episode triggers (start of episode trigger duration 912) after the start day 918 and before the end day 920 and therefore is a child of the parent episode. The third potential child episode triggers (start of episode trigger duration 916) before the start day 918 and therefore cannot be a child of the parent episode. Note that the potential child episode must only start or begin within the overlap period 922 and do not have to finish before the end day.

FIG. 9B illustrates another example of a timing diagram 950 with the overlap period 970, having start day 966 and end day 968 for the parent episode defined in the association information. As similarly discussed above, the parent episode has episode duration 952 and the three potential child episodes have episode durations 956, 960 and 964. In this example, the start day 966 and the end day 968 correspond with the parent episode's episode duration 954, as defined in association information.

As previously discussed above, a potential child episode must trigger within the overlap period 970 to be a child of the parent episode. In illustrated example of FIG. 9B the first potential child episode triggers after the end day 968 and therefore is not a child of the parent episode. The second potential child episode triggers within the overlap period 970 and is a child of the parent episode. Note that the second potential child episode finishes after the end day 968 as shown by trigger duration 962. As mentioned, the potential child episode only needs to start within the overlap period 970 and does not have to finish with the overlap period 970 to be a child of the parent episode. The third potential child episode triggers before the start day 966 and therefore is not a child episode of the parent.

FIGS. 9A and 9B illustrate example timing diagrams 900 and 950 to show when a potential episode is required to trigger such that it may be a child of a parent episode. Embodiments are not limited to these examples. Further, during processing and generation of the candidate episode pairs list, each candidate episode pairs may be analyzed to determine whether the potential child episode triggers within the overlap duration for the parent episode. Candidate episode pairs that have children that do not trigger within the overlap duration are removed from the candidate episode pairs list.

Figure 10A:
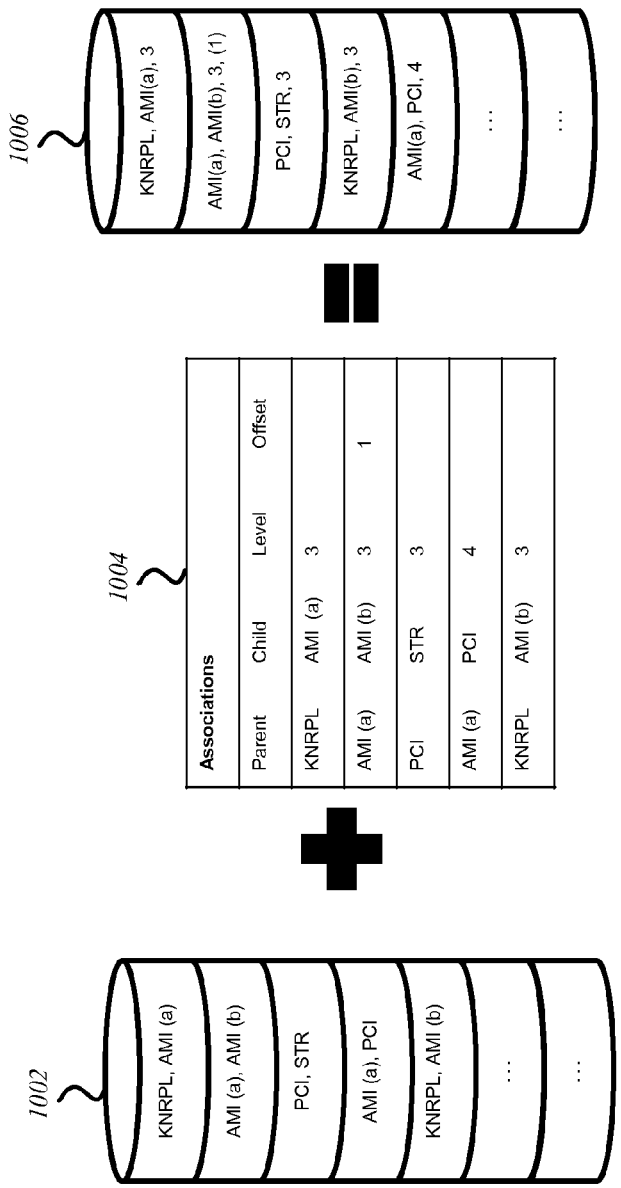
FIGS. 10A-10C illustrate example diagrams for determine association a level adjustment.
Figure 10B:
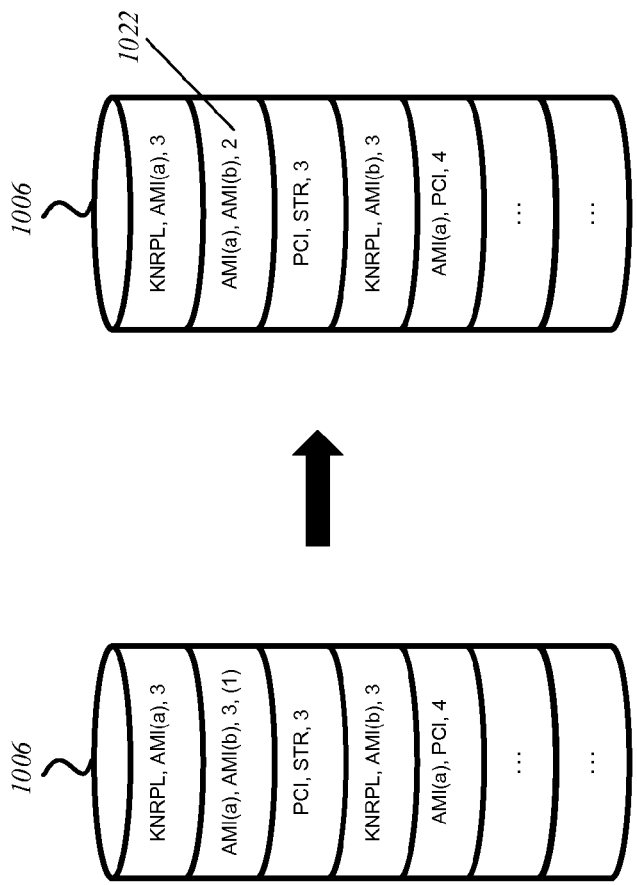
Figure 10C:
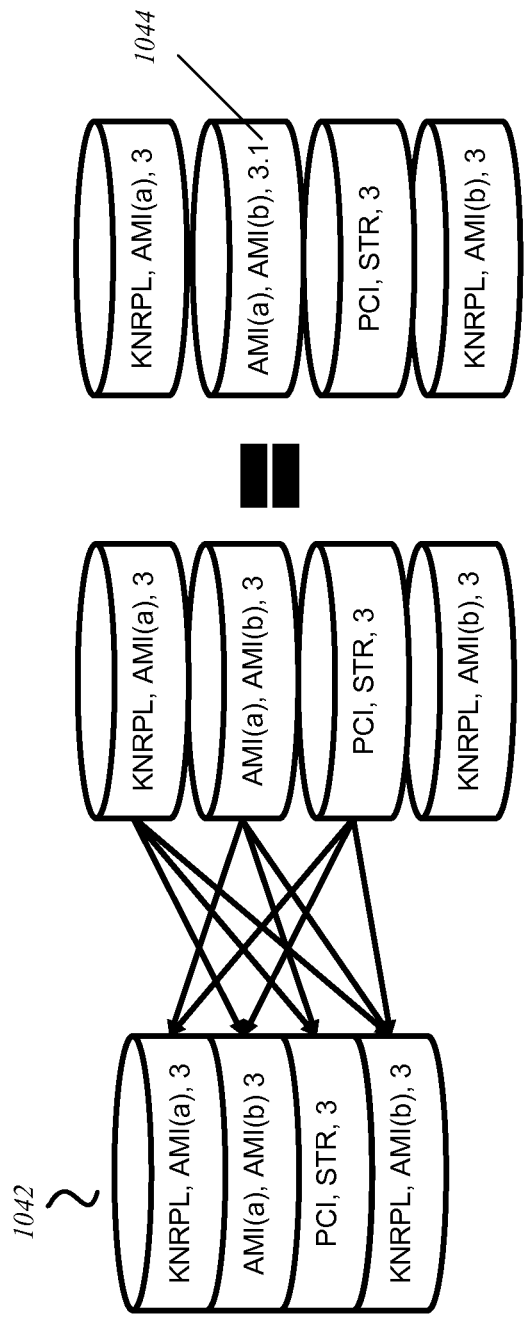

FIGS. 10A-10C illustrate example embodiments of processing diagrams 1000, 1020 and 1040 for determining and calculating association level adjustments. As previously mentioned, an association level for candidate episode pairs in the candidate episode pairs list may be adjusted by performing an offset operation (FIG. 10B) or stacking operation (FIG. 10C). These adjustments may be made to association levels for each candidate episode pair having a parent episode that is a child episode in another candidate episode pair at the same association level. Please note that the example illustrated in FIGS. 10A-10C is independent from the examples illustrated in FIGS. 6-9B.

FIG. 10A illustrates an example of a candidate episode pairs list 1002 evaluated against example association information 1004 to generate a candidate episode pairs list 1006 with association levels and offset values. FIG. 10A illustrates episode pairs in the candidate episode pairs list 1002 in a (parent, child) configuration and in the generated candidate episode pairs list 1006 as (parent, child, association level, offset value) configuration. As illustrated in FIG. 10A, the candidate episode pairs (KNRPL, AMI(a)), (AMI(a), AMI(b)), and (PCI, STR) have an association level of three (3). The candidate episode pair (AMI(a), AMI(b)) has an offset value of one (1). Once an association level for each candidate episode pair is determined, an offset operation or stacking operation may be performed to adjust association levels for each candidate episode pair having a parent episode that is a child episode in another candidate episode pair at the same association level.

To perform the adjustment using the offset operation a determination is made as to whether a candidate episode pair including a parent episode that is a child episode in another candidate episode pair at the same association level includes an offset adjustment value in the association information. In FIGS. 10A and 10B, AMI(a) is both a parent and a child episode at an association level of three (3), and the candidate episode pair (AMI(a), AMI(b)) includes an offset value of one (1). The offset value of one (1) is subtracted from the association level of three (3) to generate a new association level of two (2) for the candidate episode pair (AMI(a), AMI(b)), as illustrated in FIG. 10B at indicator 1022. In the illustrated example, no other episodes are both a parent and child at the same association level. Therefore, no other association level adjustments are required in this example.

As alternative to the offset operation, a stacking operation may be performed to adjust the association level for candidate episode pair having a parent episode that is a child episode in another candidate episode pair, as illustrated in FIG. 10C. Note that the stacking operation illustrated in FIG. 10C uses different episodes pairs and association levels than the offset example of FIG. 10B for simplicity reasons. The stacking operation uses the candidate episode pairs list 1042 and each candidate episode pair at a particular association level, three (3) in this example, to determine if a parent episode in a candidate episode pair is a child episode of another candidate episode pair at the same association level. The candidate episode pair with the parent episode is identified as being 'stacked'. Each episode of each candidate episode pair is compared to all of the other episodes in the candidate episode pairs 1042 at the same association level as indicated by the arrows. Each episode identified as being stacked increments its association level by a decimal value, such as 0.1, 0.01, 0.001, etc., depending on need. Thus, if the association level for a candidate episode pair is three (3), as is the case for (AMI(a), AMI(b)), the new association level for the stacked candidate episode becomes 3.1, as illustrated by indicator 1044. In this example, no other candidate episode pairs 1042 require association level adjustment. However, this process may be repeated any number of times so that no episodes are parents and children at the same association level.

Figure 11A:
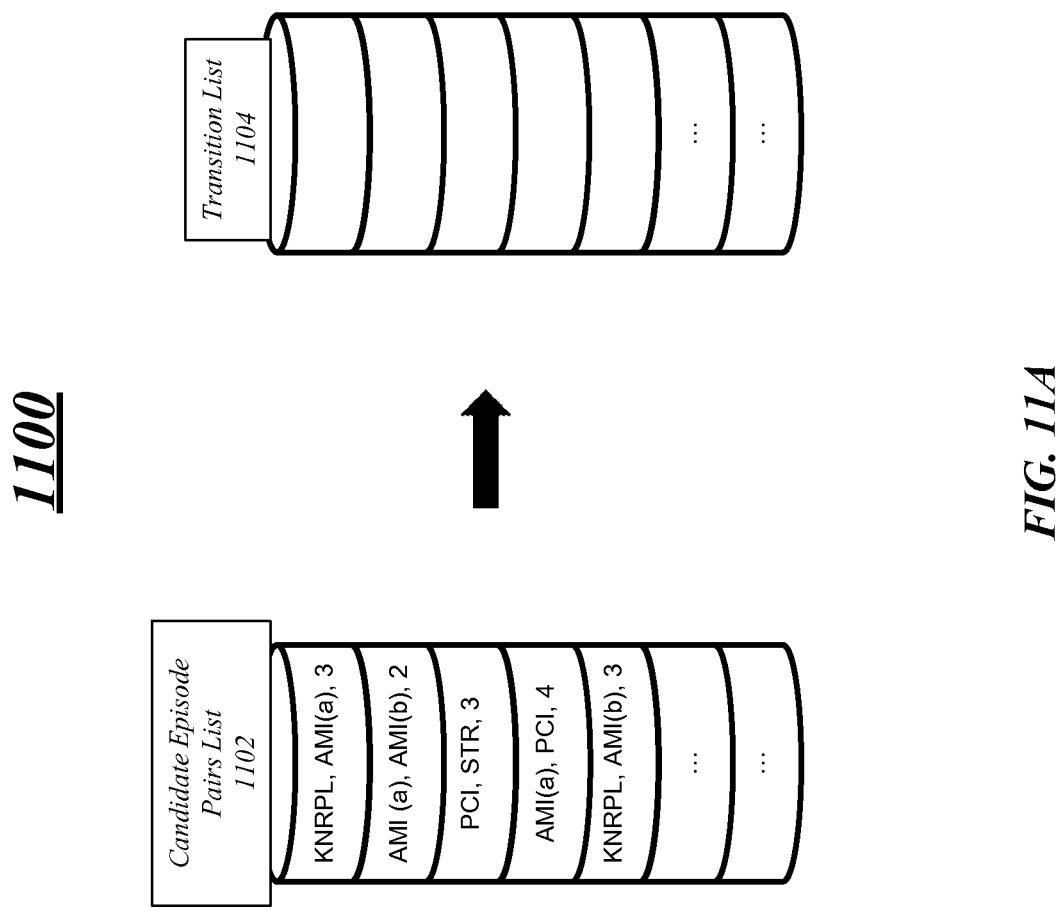

FIGS. 11A-11D illustrate an example embodiment of processing flow diagrams 1100, 1110, 1120 and 1130 to generate a transition list from a candidate episode pairs list. FIG. 11A illustrates a candidate episode pairs list 1102 and a transition list 1104 prior to generating and adding any candidate episode pairs to the transition list 1104. As previously mentioned, the candidate episode pairs will be added to the transition list 1104 starting with pairs having the lowest association level and increasing in association level until all of the candidate episode pairs have been processed. Please note that the candidates episode pairs list 1102 includes the same candidate episode pairs illustrated in FIG. 10B, but not FIG. 10C.

Figure 11B:
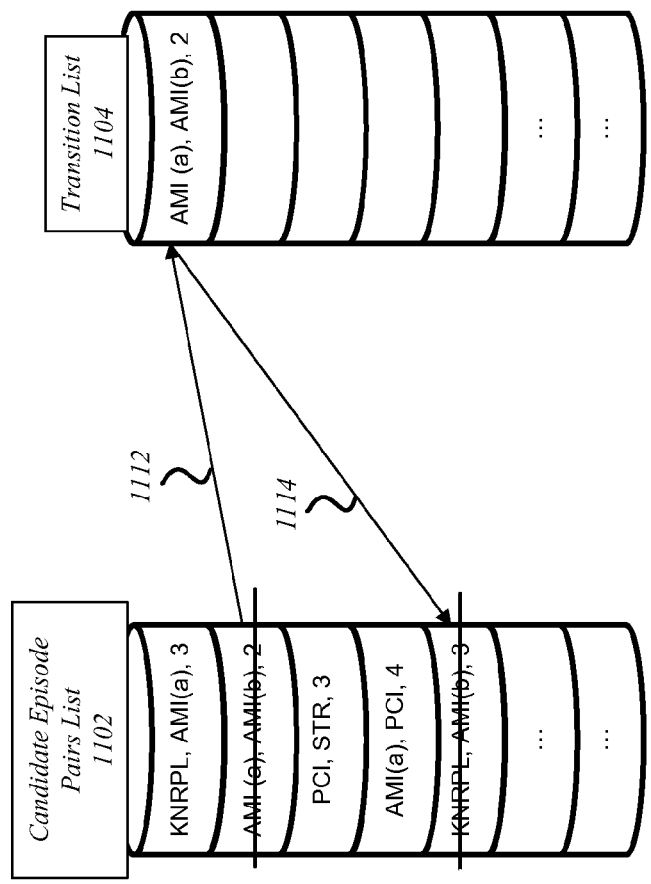

FIG. 11B illustrates candidate episode pair (AMI(a), AMI(b)) having the lowest association level of two (2) being added to the transition list 1104 at line 1112. After a candidate episode pair is added to the transition list each remaining candidate episode pair at a higher association level having a child episode that is a child episode of the newly added episode pair is removed from the candidate episode pairs list 1102 as illustrated at line 1114. The candidate episode pair (KNRPL, AMI(b)) is removed because AMI(b) is a child of episode pair (AMI(a), AMI(b)) in the transition list at a lower association level. The removed candidate episode pairs are not added to the transition list 1104. This process would be repeated for each candidate episode pair at level two (2). Once all the candidate episode pairs at the same association level, two (2) in this case, are added to the transition list 1104, the association level is increased to the next lowest association level. The remaining candidate episode pairs in the candidate episode pairs list 1102 at the next lowest association level are then added to the transition list 1104.

Figure 11C:
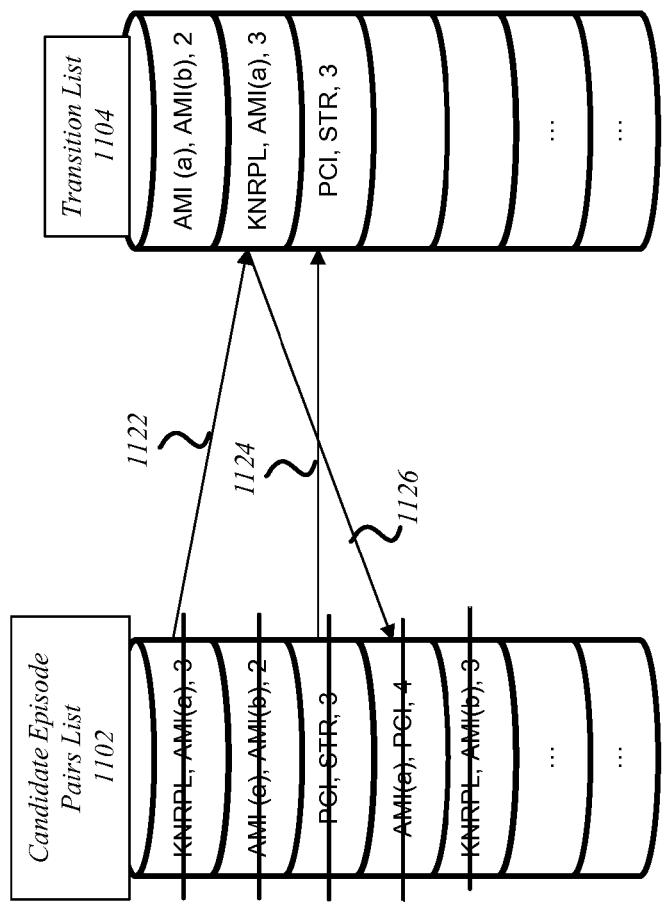

For example, FIG. 11C illustrates candidate episode pairs at the association level of three (3) being added to the transition list 1104 at lines 1122 and 1124. After each candidate episode pair is added to the transition list 1104, each remaining candidate episode pair in the candidate episode pairs list 1102 at a higher association level having a child episode that is a child episode of the newly added episode pair is removed from the candidate episode pairs list 1102, as previously discussed. In this example, the added episode pair (KNRPL, AMI(a)) has a child episode that is a child episode of candidate episode pair (AMI(a), PCI) at association level four (4). Therefore, the candidate episode pair (AMI(a), PCI) is removed from candidate episode pairs list 1102. In this example, no other candidate episode pairs remain in the candidate episode pairs list 1102. However, if candidate episode pairs remained in the candidate episode pairs list 1102, this process would repeat.

After all the candidate episode pairs have been processed, the transition list 1104 is finalized by adding transition identity pairs 1152 to the transition list 1104 to generate a final transition list 1154 as illustrated in FIG. 11D. Each remaining episode in the transition list 1104 will have an identity episode pair added to generate the finalized transition list 1154. For example, FIG. 11D illustrates identity episode pairs (AMI(a), AMI(a)) (AMI(b), AMI(b)), (PCI, PCI), (KNRPL, KNRPL), and (STR, STR) being added to generate the finalized transition list 1154. Further, these identity episode pairs are added to the finalized transition list 1154 with a lowest association level, e.g. one (1) in this example. As will be discussed in more detail below, these identity episode pairs will be used to determine the relationships between the episodes.

Figure 12A:
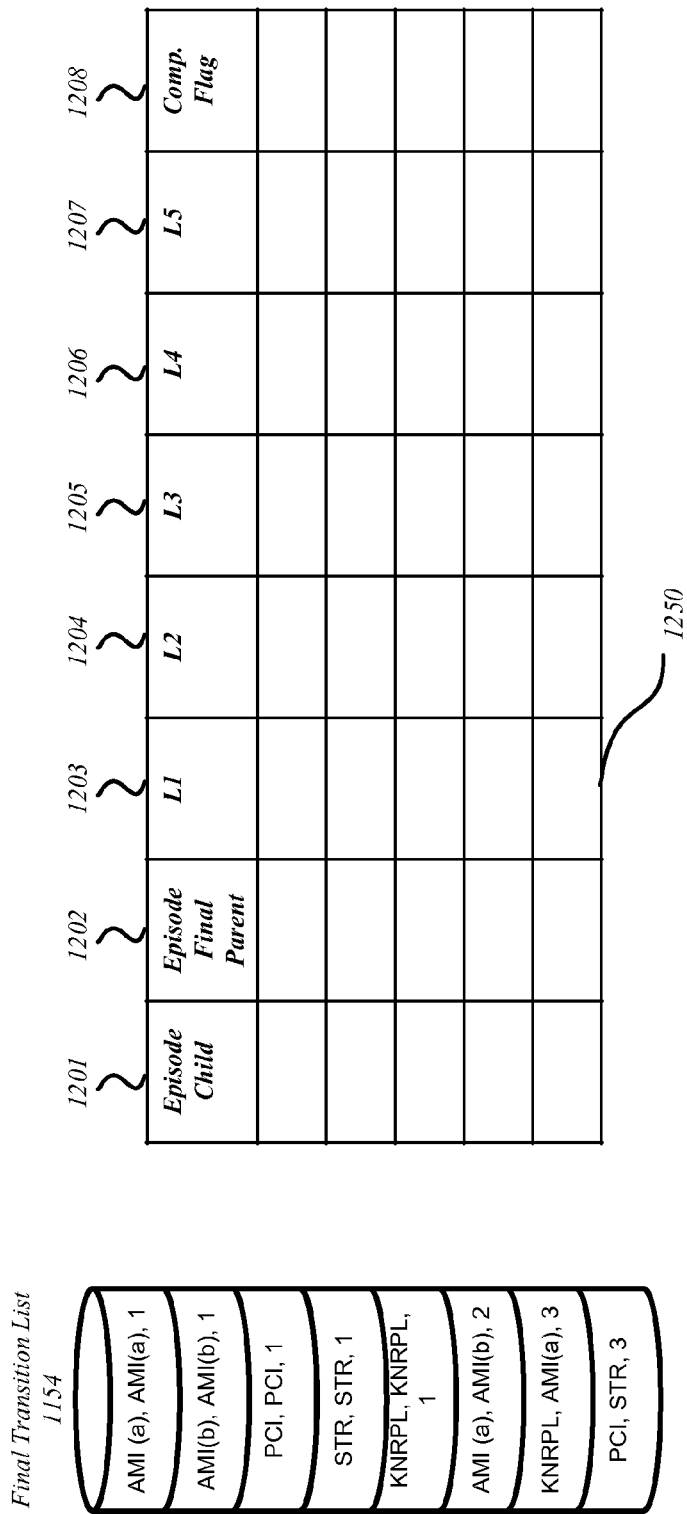

FIGS. 12A-12E illustrate an embodiment of a leveling process 1200 to generate relationships shown in table 1250 during a leveling operation. FIG. 12A illustrates a table 1250 having a number of columns including an episode child 1201, an episode final parent 1202, levels L1-L5 in columns 1203-1207, and a completion flag 1208. The completion flag 1208 column holds a value indicating that all relevant care for an episode is captured. For example, a value of one (1) in the completion flag 1208 may indicate that the all of the records for a particular episode are available and a total cost may be determined. The level L1-L5 columns 1203-1207 hold weighted values and represent association levels for episode pairs. Thus, L1 indicates an association level of one (1), L2 indicates an association level of two (2), and so forth. In some embodiments, the weighted value may be any number from zero (0) to one (1), where a weighted value greater than zero (0) represents that a child episode and a parent episode of the episode pair have some attribute relationship at that particular association level. In some embodiments, a weighted value of one (1) indicates that an attribute item, such as cost, complication, pharmaceutical prescription, and so forth, of a child episode may be entirely attributed to the parent episode. A weight value between zero (0) and one (1) may indicate that a fraction of the item of a child episode may be attributed to the parent episode and a weighted value of zero (0) may indicate that a child episode does not have an attribute relationship with the parent episode at that particular association level.

Figure 12B:
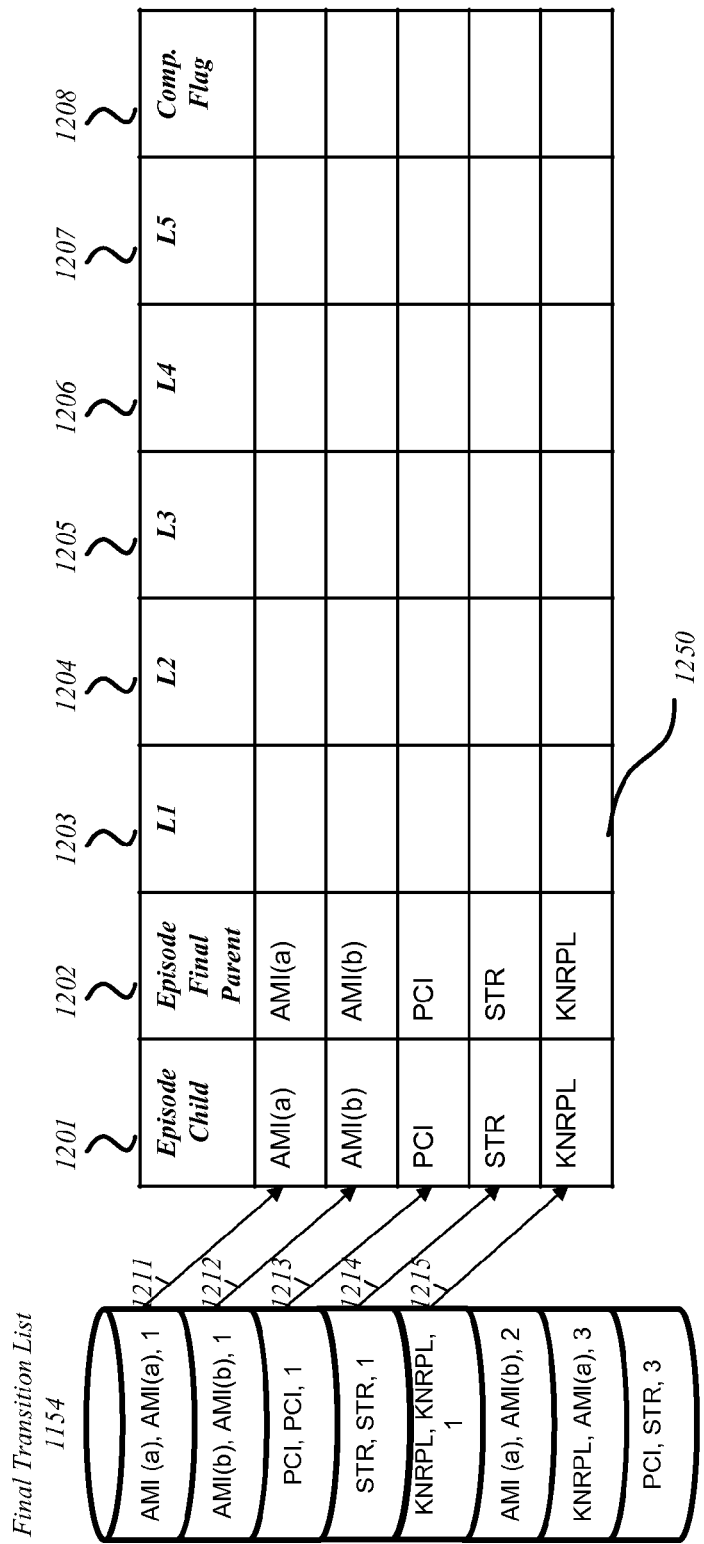
Figure 12C:
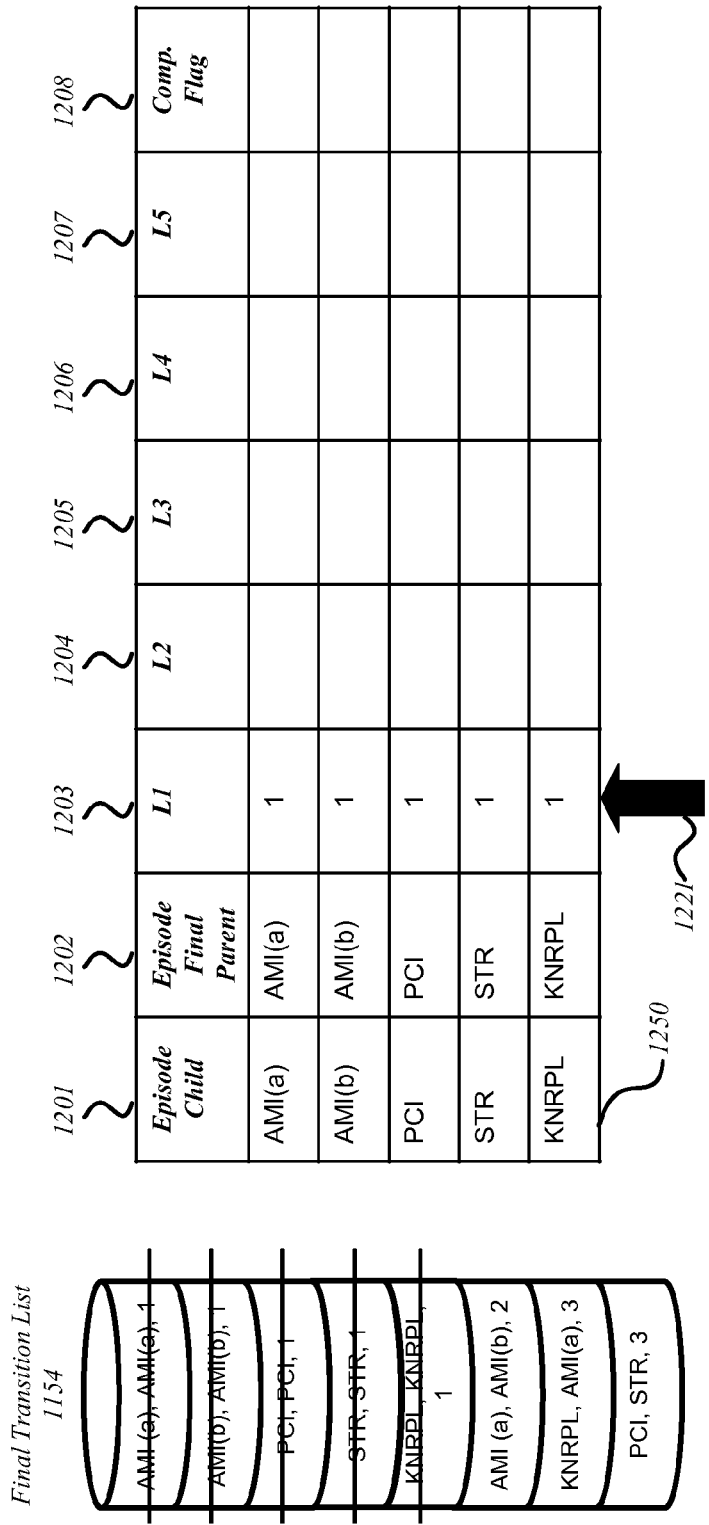

FIG. 12B illustrates the table 1250 being populated with the identity episode pairs from the final transition list 1154 at lines 1211-1215. As previously mentioned, each episode in the final transition list 1154 will have an identity episode pair. Once these identity episode pairs are added to the table 1250, they may be removed from the final transition list 1154 as illustrated in FIG. 12C. Further, a weighted level value may be added in the level L1 column 1203 for each of the identity episode pairs as identified by indicator 1221. In this example, a level value of one (1) is added to the table 1250. The weighted level value of one (1) in the level L1 column 1203 indicates that an attribute relationship exists between the episode child and the parent episode for the episode pair at level L1. Thus, in one example the costs of the child episode are attributed to the costs of the parent episode, which in this case is itself. Once the identity episode pairs having an association level of one (1) are inserted into the table 1250, episode pairs at the next higher association level may be evaluated and inserted into the table 1250.

Figure 12D:
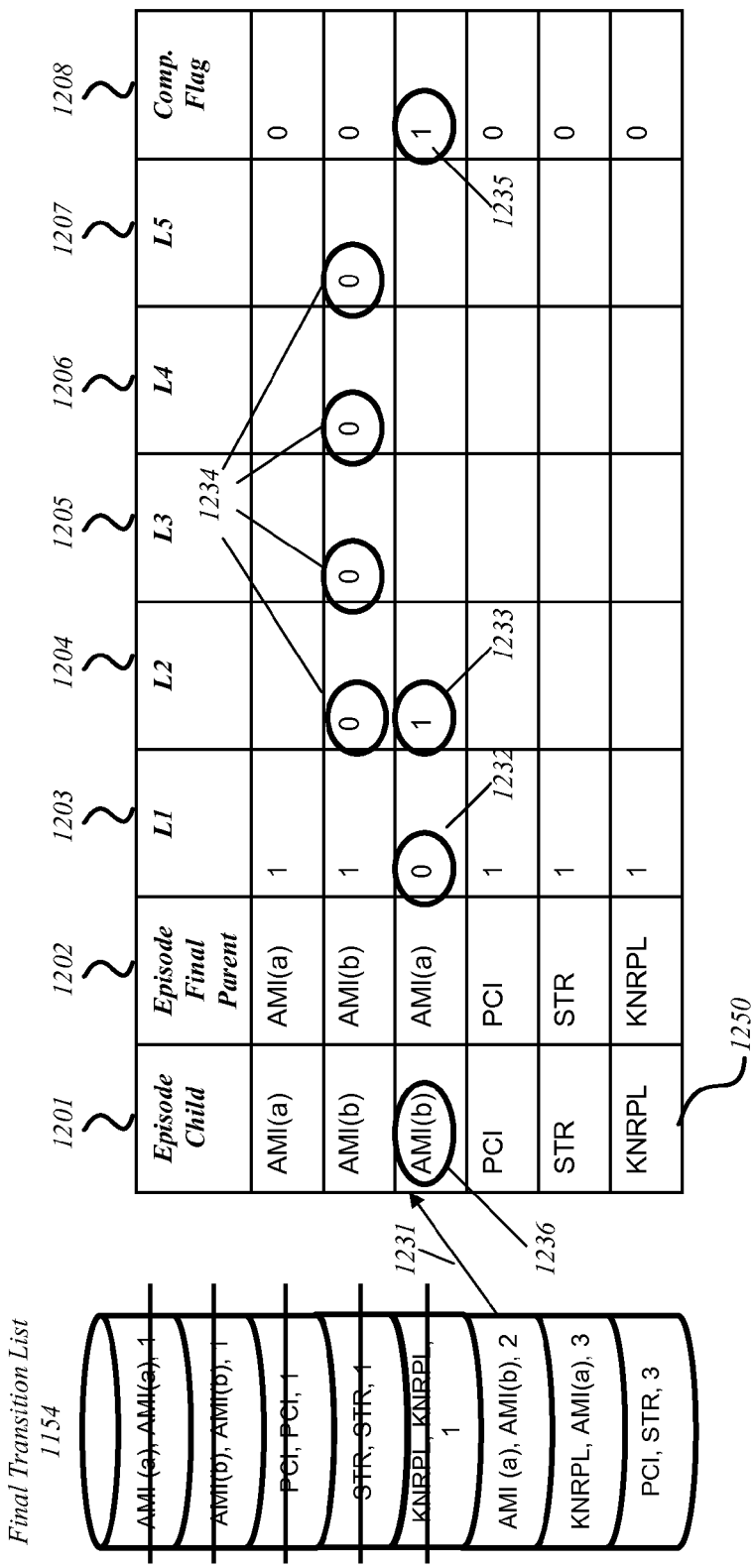

FIG. 12D illustrates the episode pair (AMI(a), AMI(b)) having an association level of two (2) being inserted in the table 1250 from the final transition list 1154 at line 1231. As illustrated in FIG. 12D, each episode pair added to the table 1250 may be inserted after an episode pair having a parent episode that is a child episode of the episode pair being added. In addition, the child episode of the episode pair being added is replaced with the child episode of the episode pair directly above the added episode pair as identified by identifier 1236. In this case, the episode pair (AMI(a), AMI(b)) is being inserted into the table after identity episode (AMI(b), AMI(b)) at line 1231. Thus, child episode AMI(b) is replaced with the child episode of the identity pair (AMI(b), AMI(b)) and the child episode remains the same. However, this is not always the case, as will become apparent. Further, each episode pair in the final transition list 1154 at the same association level may be inserted into the table 1250 during the same processing cycle. In this example, only one episode pair has an association level of two (2) and is being inserted into table 1250. However, embodiments are not limited in this manner and any number of episode pairs may be inserted into the table 1250 at a specific association level being processed.

In addition to inserting episode pairs into the table 1250, the level L1-L5 columns 1203-1207 may be updated with weighted level values. In embodiments, a weighted level value may be inserted into one of the columns 1203-1207 corresponding with the association level for the newly added episode pairs. For example, a weighted level value of one (1) is inserted into the table 1250 in the level L2 column 1204 for episode pair (AMI(a), AMI(b)) at indicator 1233. This indicates, that an attribute relationship exists between child episode AMI(b) and parent episode AMI(a) at association level two (2). Thus, in one example, the costs of AMI(b) may be attributed to the costs of AMI(a) at association level two (2).

In addition, a weighted level value of zero (0) may be inserted into the table 1250 for all of the preceding or lower level L#'s for the newly added episode pair(s), e.g. as shown for episode pair (AMI(a), AMI(b)) at line 1232. Similarly, a weighted value may be inserted into the table 1250 in open level L# columns 1203-1207 for any episode pair that has a same child episode as the child episode of the newly added episode pair. For example, a zero (0) may be entered into level L2-L5 columns 1204-1207 for identity episode pair (AMI(b), AMI(b)) as indicated by indicators 1234. The zero (0) value in table 1250 for this episode pair indicates that a attribute relationship no longer exists between the child and parent episode pair at these particular association levels, e.g. two (2) through five (5). In addition, a value of one (1) may be entered into the table 1250 for the newly added episode pair, (AMI(a), AMI(b)) in the completion flag 1208 as indicated by indicator 1235. Once all of the episode pairs from the final transition list 1154 are added to the table 1250 at a particular association level, the episode pairs added to the table 1250 may be removed from the final transition list 1154. The association level is increased and the remaining episode pairs in the final transition list 1154 are processed.

Figure 12E:
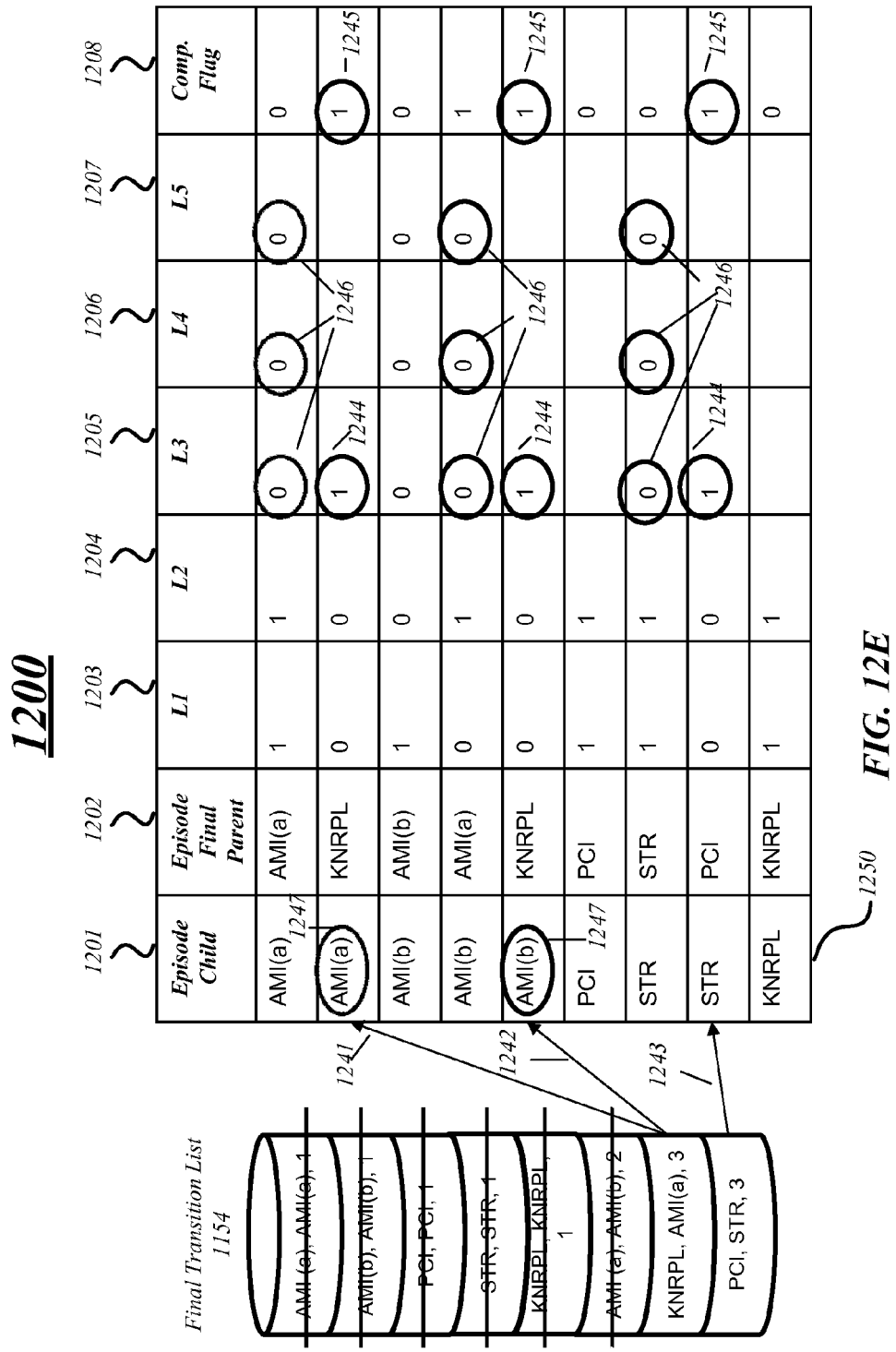

FIG. 12E illustrates episode pairs, (KNRPL, AMI(a)) and (PCI, STR), being added to the table 1250 at lines 1241, 1242 and 1243. As previous mentioned, each episode pair from the final transition list 1154 is inserted in the table 1250 after each episode pair in the table having a parent that is a child of the episode pair being added. Thus, in this example, the episode pair (KNRPL, AMI(a)) is added to the table 1250 after episode pairs (AMI(a), AMI(a)) and (AMI(a), AMI(b)), as can be illustrated by lines 1241 and 1242. Each of the child episode(s) of the newly added episode(s) is then updated or replaced with the child episode directly above it in the table. For example, at indicators 1247 each of the child episodes are replaced with the child episode from directly above. More specifically, child episode AMI(a) associated with line 1241 is replaced with child episode AMI(a), which is the same in this case because the episode pair directly above the newly added episode pair is the identity episode pair (AMI(a), AMI(a)). Further, the child episode AMI(a) associated with line 1242 is replaced with child episode AMI(b) from the episode pair (AMI(a), AMI(b)) directly above the newly added episode pair. Replacing the child episodes when the inserting episode pairs into table 1250 ensures correct attribute relationships and attribute items of a child episode are attributed to the correct parent episode at a particular level. As can be seen from table 1250, the KNRPL is a parent of AMI(a), and AMI(a) is a parent of AMI(b). Thus, the KNRPL is the parent of AMI(b) at a certain association levels, three (3) for example.

In a similar manner, the episode pair (PCI, STR) is inserted into table 1250 at line 1243 and its child episode (STR) is replaced with the child episode directly above it. In this example, the episode pair directly above the newly added episode pair (PCI, STR) is the identity episode pair (STR, STR), and therefore, the child episode remains the same. Once the episode pairs at a particular association level are added to the table 1250, the level L1-L5 columns 1203-1207 are updated. A weighted value is put in the table at the association level for each of the newly added episode pair. In this example, a weighted value of one (1) is inserted into the table in the L3 column 1205 as shown by indicators

1244. The weighted value of one (1) indicates that an attribute relationship exists between the parent episode and the child episode at that particular association level, three (3) for example. In addition a weighted value of zero (0) in inserted in lower level columns for the newly added episode pairs. Thus, a weighted value of zero (0) is inserted into the L1 column 1203 and L2 column 1204 for the newly added episode pairs since no attribute relationship exists for the episode pairs at these levels.

In some embodiments, certain level L1-L5 columns 1203-1207 may also be filled with weighted values. For example, episode pairs having a child episode that now has a new parent episode at a higher association level may receive weighted values of zero (0) in the table 1250, as illustrated by indicator 1246. For example, the child episode of episode pair (AMI(a), AMI(b)) has a new parent episode at association level three (3), and therefore, will receive weighted value of zero (0) in levels L3-L5 columns 1205-1207. In addition, a completion flag in column 1208 may be set for newly added episode pairs (KNRPL, AMI(a)), (KNRPL, AMI(b)), and (PCI, STR) as illustrated by indicator 1245. The leveling process may be repeated any number of times for each association level until no episode pairs remain in the final transition list 1154. In the current example, no episode pairs remain in the transition list after association level three (3). However, embodiments are not limited in this manner and any number of association levels may exist.

Once no episode pairs remain in the final transition list 1154, the remaining columns and row of the table 1250 may be filled in with weighted values. In some embodiments, a weighted value of one (1) may be inserted into the table 1250 having open spaces. Thus, as illustrated in FIG. 12F, the remaining rows 1252-1260 having open spaces for the episodes are completed by filling in the open spaces with an weighted value of one (1). This indicates that the episode pair's child and parent episodes have an attribute relationship at the particular association levels corresponding to the remaining levels L1-L5 columns 1203-1207. In this example, the leveling process is complete and the table 1250 is completely filled with values. Embodiments are not limited to this example and may include any number of episode pairs, association levels, and so forth.

In some embodiments, the information in the table 1250 including the weighted values may be used by a device or a person to determine attribute relationships between episodes for a person or patient. For example and with reference to table 1250 in FIG. 12F, a device may use the information in table 1250 to determine that at association level 3 corresponding to level L3 column 1205, a patient has a number of episodes having attribute relationships including episode pairs (KNRPL, AMI(a)), (KNRPL, AMI(a)), (PCI, PCI), (PCI, STR), and (KNRPL, KNRPL). These episode pairs all have an attributed relationship indicating that an attribute item of a child episode may be attributed to the parent episode. As can be apparent from one skilled in the art, attribute relationships can be determined for any of the episode pairs at any association level based on the information in the table 1250. Further, the table 1250 may indicate what episodes "exist" at a specific level. For example, at association level 3, table 1250 illustrates that a PCI exists which is a combination of the original PCI and the STR. Also, there is a KNRPL that is the sum total of the original KNRPL plus two AMI (a and b). In another example, the table 1250 may be used to determine a root cause of a particular episode. In one specific example, the root cause of AMI(b) may be determined to be the KNRPL based on the KNRPL causing the AMI(a) which caused the AMI(b). Embodiments are not limited in this manner.

In some embodiments, the information in the table 1250 may be presented to a user in a table format, as found in FIGS. 12A-12D and/or in number of other different formats. For example, the information in the table 1250 may be used to generate one or more graphs capable of being displayed on a computing display device. These graphs may include additional information, such as attribute items and may illustrate the flow of attribute items from a parent episode to a child episode, or vice versa, at particular association level.

Figure 13:
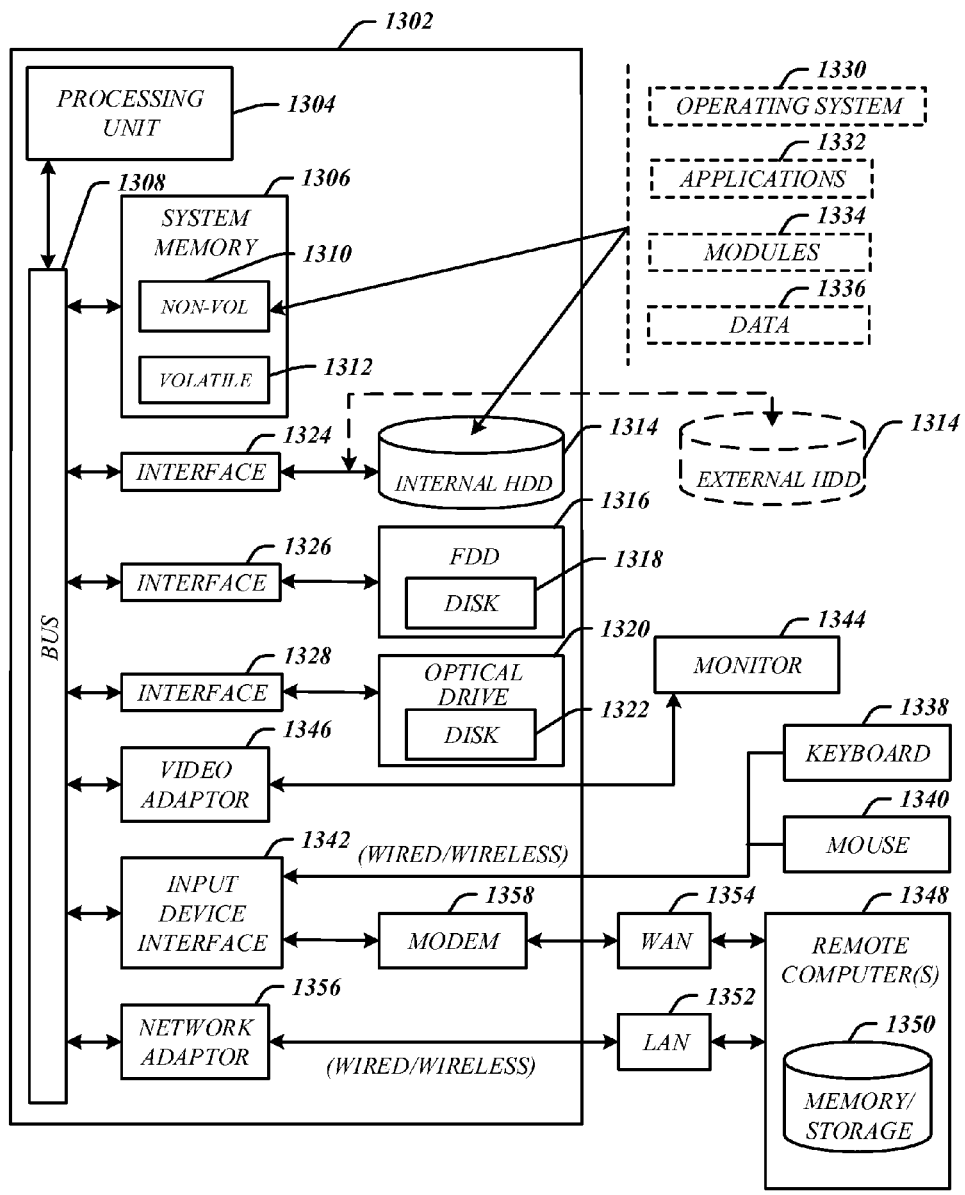
FIG. 13 illustrates an exemplary embodiment of a computing architecture.

FIG. 13 illustrates an embodiment of a computing architecture 1300 suitable for implementing various embodiments as previously described. More specifically, various aspects and/or portions of computing architecture 1300 (or variants thereof) may be implemented as part of one or more systems, devices, embodiments and so forth to implement various particular features discussed above with respect to FIGS. 1-12F. In one embodiment, one or more devices of computing architecture 1300 may implemented as part of system 100 and sub-system 150 of FIGS. 1A and 1B. Further, various components of computer architecture 1300 may be used to implemented or enable any one of the processing flows previously discussed. Embodiments are not limited in this manner.

Components may be communicatively coupled to each other by various types of communications media to coordinate operations. The coordination may involve the uni-directional or bi-directional exchange of information. For instance, the components may communicate information in the form of transmissions communicated over the communications media. The information can be implemented as transmissions allocated to various transmission lines. In such allocations, each message is a transmission. Further embodiments, however, may alternatively employ data messages. Such data messages may be sent across various connections. Exemplary connections include parallel interfaces, serial interfaces and bus interfaces.

The computing architecture 1300 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies and so forth. The embodiments, however, are not limited to implementation by the computing architecture 1300.

As shown in FIG. 13, the computing architecture 1300 comprises a processing unit 1304, a system memory 1306 and a system bus 1308. The processing unit 1304 can be any of various commercially available processors. Processing unit 1304 may be one or more of any type of computational element, such as but not limited to, a microprocessor, a processor, central processing unit, digital signal processing unit, dual core processor, mobile device processor, desktop processor, single core processor, a system-on-chip (SoC) device, complex instruction set computing (CISC) microprocessor, a reduced instruction set (RISC) microprocessor, a very long instruction word (VLIW) microprocessor, or any other type of processor or processing circuit on a single chip or integrated circuit. The processing unit 1304 may be connected to and communicate with the other elements of the computing system via an interconnect. Further, processing unit 1304 may include other components, such as an uncore component including logic to process information, instructions and so forth not essential to core processing.

The system bus 1308 provides an interface for system components including, but not limited to, the system memory 1306 to the processing unit 1304. The system bus 1308 can be any of several types of bus structure that may further interconnect to a memory bus (with or without a memory controller), a peripheral bus and a local bus using any of a variety of commercially available bus architectures. Interface adapters may connect to the system bus 1308 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA) and the like.

The computing architecture 1300 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory and so forth. Examples of logic may include executable computer program instructions implemented using any suitable type of code, such as source code, compiled code, interpreted code, executable code, static code, dynamic code, object-oriented code, visual code and the like. Embodiments may also be at least partly implemented as instructions contained in or on a non-transitory computer-readable medium, which may be read and executed by one or more processors to enable performance of the operations described herein.

The system memory 1306 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 13, the system memory 1306 can include non-volatile memory 1310 and volatile memory 1312. A basic input/output system (BIOS) can be stored in the non-volatile memory 1310.

The computer 1302 may include various types of computer-readable storage media in the form of one or more lower speed memory units, including an internal (or external) hard disk drive (HDD) 1314, a magnetic floppy disk drive (FDD) 1316 to read from or write to a removable magnetic disk 1318 and an optical disk drive 1320 to read from or write to a removable optical disk 1322 (e.g., a CD-ROM or DVD). The HDD 1314, FDD 1316 and optical disk drive 1320 can be connected to the system bus 1308 by a HDD interface 1324, an FDD interface 1326 and an optical drive interface 628, respectively. The HDD interface 1324 for external drive implementations can include at least one or both of Universal Serial Bus (USB) and IEEE 1394 interface technologies.

The drives and associated computer-readable media provide volatile and/or nonvolatile storage of data, data structures, computer-executable instructions and so forth. For example, a number of program modules can be stored in the drives, non-volatile memory 1310 and volatile memory 1312, including an operating system 1330, one or more application programs 1332, other program modules 1334 and program data 1336. In one embodiment, the one or more application programs 1332, other program modules 1334 and program data 1336 can include, for example, the various applications and/or components of system 100 and leveling processing sub-system 110.

A user can enter commands and information into the computer 1302 through one or more wire/wireless input devices, for example, a keyboard 1338 and a pointing device, such as a mouse 1340. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses and the like. These and other input devices are often connected to the processing unit 1304 through an input device interface 1342 that is coupled to the system bus 1308, but can be connected by other interfaces such as a parallel port, IEEE 1394 serial port, a game port, a USB port, an IR interface and so forth.

A monitor 1344 or other type of display device is also connected to the system bus 1308 via an interface, such as a video adaptor 1346. The monitor 1344 may be internal or external to the computer 1302. In addition to the monitor 1344, a computer typically includes other peripheral output devices, such as speakers, printers and so forth.

The computer 1302 may operate in a networked environment using logical connections via wire and/or wireless communications to one or more remote computers, such as a remote computer 1348. The remote computer 1348 can be a workstation, a server computer, a router, a personal computer, portable computer, microprocessor-based entertainment appliance, a peer device or other common network node and typically includes many or all of the elements described relative to the computer 1302, although, for purposes of brevity, only a memory/storage device 1350 is illustrated. The logical connections depicted include wire/wireless connectivity to a local area network (LAN) 1352 and/or larger networks, for example, a wide area network (WAN) 1354. Such LAN and WAN networking environments are commonplace in offices and companies and facilitate enterprise-wide computer networks, such as intranets, all of which may connect to a global communications network, for example, the Internet.

When used in a LAN networking environment, the computer 1302 is connected to the LAN 1352 through a wire and/or wireless communication network interface or adaptor 1356. The adaptor 1356 can facilitate wire and/or wireless communications to the LAN 1352, which may also include a wireless access point disposed thereon for communicating with the wireless functionality of the adaptor 1356.

When used in a WAN networking environment, the computer 1302 can include a modem 1358, or is connected to a communications server on the WAN 1354, or has other means for establishing communications over the WAN 1354, such as by way of the Internet. The modem 1358, which can be internal or external and a wire and/or wireless device, connects to the system bus 1308 via the input device interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with wire and wireless devices or entities using the IEEE 802 family of standards, such as wireless devices operatively disposed in wireless communication (e.g., IEEE 802.11 over-the-air modulation techniques). This includes at least WiFi (or Wireless Fidelity), WiMax and Bluetooth™ wireless technologies, 3G, 4G, LTE wireless technologies, among others. Thus, the communication can be a predefined structure as with a conventional network or simply an ad hoc communication between at least two devices. WiFi networks use radio technologies called IEEE 802.11x (a, b, g, n, etc.) to provide secure, reliable, fast wireless connectivity. A WiFi network can be used to connect computers to each other, to the Internet and to wire networks (which use IEEE 802.3-related media and functions).

Some systems may use Hadoop®, an open-source framework for storing and analyzing big data in a distributed computing environment. Some systems may use cloud computing, which can enable ubiquitous, convenient, on-demand network access to a shared pool of configurable computing resources (e.g., networks, servers, storage, applications and services) that can be rapidly provisioned and released with minimal management effort or service provider interaction. Some grid systems may be implemented as a multi-node Hadoop® cluster, as understood by a person of skill in the art. Apache™ Hadoop® is an open-source software framework for distributed computing. Some systems may use the SAS® LASR™ Analytic Server in order to deliver statistical modeling and machine learning capabilities in a highly interactive programming environment, which may enable multiple users to concurrently manage data, transform variables, perform exploratory analysis, build and compare models and score with virtually no regards on the size of the data stored in Hadoop®. Some systems may use SAS In-Memory Statistics for Hadoop® to read big data once and analyze it several times by persisting it in-memory for the entire session.

The various elements of the computer systems as previously described with reference to FIGS. 1-5 may involve determining whether an embodiment is implemented using hardware elements and/or software elements, which may vary in accordance with any number of factors, such as desired computational rate, power levels, heat tolerances, processing cycle budget, input data rates, output data rates, memory resources, data bus speeds and other design or performance constraints, as desired for a given implementation.

What is claimed is:

1. An apparatus, comprising:
 processing circuitry;
 memory coupled with the processing circuitry;
 a candidate component having instructions storable in the memory and operable on the processing circuitry, the candidate component to:
  receive episode information for a patient from a storage device via one or more links, the episode information comprising a plurality of episodes associated with the patient, each of the plurality of episodes is a specific instance of a medical condition, and
  generate a candidate episode pairs list comprising a plurality of candidate episode pairs by:
   performing a Cartesian merge of the plurality of episodes, and
   comparing each of the candidate episode pairs with association information defining related medical conditions,
   each of the candidate episode pairs having a different association level and each of the candidate episode pairs define a parent-child relationship,
   each of the association levels define a relative strength between episodes in each of the candidate episode pairs;
 a transition component having instructions storable in the memory and operable on the processing circuitry, the transition component to generate a transition list comprising episode pairs from the plurality of candidate episode pairs in the candidate episode pairs list; and
 a leveling component having instructions storable in the memory and operable on the processing circuitry to determine attribute relationships between the plurality of episodes for the patient based on episode pairs in the transition list, the attribute relationships used to attribute items between the plurality of episodes.

2. The apparatus of claim 1, the candidate component to remove candidate episode pairs not defined as related medical conditions from candidate episode pairs lists based on the comparison with the association information.

3. The apparatus of claim 1, the candidate component to:
 determine whether episodes of a particular candidate episode pair overlap in time; and
 remove the particular candidate episode pair from the candidate episode pairs list based on determining that the particular candidate episode pair does not include episodes that overlap in time.

4. The apparatus of claim 1, the candidate component to adjust an association level for a first candidate episode pair having a parent episode that is a child episode in a second candidate episode pair by performing an offset operation or a stacking operation.

5. The apparatus of claim 1, the transition component to:
 iteratively add candidate episode pairs from the candidate episode pairs list to the transition list starting with candidate episode pairs with a lowest association level;
 remove each remaining candidate episode pairs from the candidate episode pairs list having a same child episode of an episode pair in the transition list;
 after each iteration, increase to a next lowest association level associated with candidate episode pairs and repeat the add and remove operations until no candidate episode pair remain in the candidate episode pair list; and
 add identity episode pairs to the transition list for each episode already in the transition list.

6. The apparatus of claim 1, the relative strength between episodes to indicate a likelihood of one episode causing another episode, a lower association level for the relative strength to indicate a higher likelihood than a higher association level.

7. The apparatus of claim 1, the leveling component to determine the attribute relationships by iteratively performing a leveling operation for each episode pairs in the transition list, the leveling operation to determine a parent episode for each child episode of each episode pair in the transition list at a particular association level.

8. The apparatus of claim 7, the leveling operation to start with one or more identity episode pairs in the transition list and add each episode pair to a table, evaluate each episode pair at each association level, and increase by association level until no episode pairs remain in the transition list.

9. The apparatus of claim 7, the leveling operation to determine a number of times each episode is a child episode at the particular level, and calculate a weighted level value for each episode pair used to determine the attribute relationships between episodes, the attribute relationships comprising a cost association for the episodes.

10. The apparatus of claim 1, comprising:
an interface coupled with the memory and the processing circuitry, the interface to receive the episode information from a remote device or a local device.

11. The apparatus of claim 1, comprising:
an interface coupled with the memory and the processing circuitry, the interface to receive the association information from a remote device or a local device.

12. At least one non-transitory computer-readable storage medium comprising instructions that when executed cause processing circuitry to:
identify episode information for a patient, the episode information comprising a plurality of episodes associated with the patient, each of the plurality of episodes is a specific instance of a medical condition;
generate a candidate episode pairs list comprising a plurality of candidate episode pairs by:
performing a Cartesian merge of the plurality of episodes, and
comparing each of the candidate episode pairs with association information defining related medical conditions,
each of the candidate episode pairs having a particular association level and each of the candidate episode pairs define a parent-child relationship,
each of the particular association levels define a relative strength between episodes in each of the candidate episode pairs;
generate a transition list comprising episode pairs from candidate episode pairs in the candidate episode pairs list; and
determine attribute relationships between the plurality of episodes for the patient based on the episode pairs in the transition list, the attribute relationships used to attribute items between the plurality of episodes.

13. The non-transitory computer-readable storage medium of claim 12, comprising instructions that when executed cause the processing circuitry to remove candidate episode pairs not defined as related medical conditions from the candidate episode pairs list.

14. The non-transitory computer-readable storage medium of claim 12, comprising instructions that when executed cause the processing circuitry to:
determine whether episodes of a particular candidate episode pair overlap in time; and
remove the particular candidate episode pair from the candidate episode pairs list based on determining that the particular candidate episode pair does not include episodes that overlap in time.

15. The non-transitory computer-readable storage medium of claim 12, comprising instructions that when executed cause the processing circuitry to adjust an association level for a first candidate episode pair having a parent episode that is a child episode in a second candidate episode pair by performing an offset operation or a stacking operation.

16. The non-transitory computer-readable storage medium of claim 12, comprising instructions that when executed cause the processing circuitry to generate the transition list, the instructions further causing the processing circuitry to:
iteratively add candidate episode pairs from the candidate episode pairs list to the transition list starting with candidate episode pairs with a lowest association level;
remove each remaining candidate episode pair from the candidate episode pairs list having a same child episode an episode pair in the transition list;
after each iteration, increase to a next lowest association level associated with candidate episode pairs and repeat the add and remove operations until no candidate episode pairs remain in the candidate episode pairs list; and
add identity episode pairs for each episode in the transition list.

17. The non-transitory computer-readable storage medium of claim 12, the relative strength between episodes to indicate a likelihood of one episode causing another episode, a lower association level for the relative strength to indicate a higher likelihood than a higher association level.

18. The non-transitory computer-readable storage medium of claim 12, comprising instructions that when executed cause the processing circuitry to determine the attribute relationships, the instructions further causing the processing circuitry to:
iteratively perform a leveling operation for each episode pair in the transition list, the leveling operation to determine a final parent episode for each child episode of each episode pair in the transition list, the final parent episode determined at a particular level.

19. The computer-readable storage medium of claim 18, the leveling operation to start with one or more identity episode pairs in the transition list and add each episode pair to a table, evaluate each episode pair at each association level, and increase by association level until no episode pairs remain in the transition list.

20. The computer-readable storage medium of claim 18, the leveling operation to determine a number of times each episode is a child episode at the particular level, and calculate a weighted level value for each episode pair for each child episode used to determine the attribute relationships between episodes, the attribute relationships comprising a cost association for the episodes.

21. A computer-implemented method, comprising:
identifying, by processing circuitry, episode information for a patient, the episode information comprising a plurality of episodes associated with the patient, each of the plurality of episodes is a specific instance of a medical condition;
generating, by the processing circuitry, a candidate episode pairs list comprising a plurality of candidate episode pairs by:
performing a Cartesian merge of the plurality of episodes, and
comparing each of the candidate episode pairs with association information defining related medical conditions,
each of the candidate episode pairs having an association level and each of the candidate episode pairs define a parent-child relationship,
each of the association levels define a relative strength between episodes in each of the candidate episode pairs;

generating, by the processing circuitry, a transition list comprising one or more episode pairs from the candidate episode pairs in the candidate episode pairs list; and determining, by the processing circuitry, attribute relationships between the plurality of episodes for the patient based on the episode pairs in the transition list, the attribute relationships used to attribute items between the plurality of episodes.

22. The computer-implemented method of claim 21, comprising removing, by the processing circuitry, candidate episode pairs not defined as related medical condition from candidate episode pairs lists.

23. The computer-implemented method of claim 21, comprising:

determining, by the processing circuitry, whether episodes of a particular candidate episode pair overlap in time; and removing the particular candidate episode pair from the candidate episodes pairs list based on determining that the particular candidate episode pair does not include episodes that overlap in time.

24. The computer-implemented method of claim 21, comprising:

adjusting the association level for a first candidate episode pair having a parent episode that is a child episode in a second candidate episode pair by performing an offset operation or a stacking operation.

25. The computer-implemented method of claim 21, comprising:

generating the transition list comprising:

iteratively adding candidate episode pairs from the candidate episode pairs list to the transition list starting with candidate episode pairs with a lowest association level;

removing each remaining candidate episode pairs from the candidate episode pairs list having a same child episode of an episode pair in the transition list; and after each iteration, increasing to a next lowest association level associated with candidate episode pairs and repeating the adding and removing operations until no candidate episode pair remain in the candidate episode pair list; and adding identity episode pairs for each episode in the transition list.

26. The computer-implemented method of claim 21, the relative strength between episodes to indicate a likelihood of one episode causing another episode, a lower association level for the relative strength to indicate a higher likelihood than a higher association level.

27. The computer-implemented method of claim 21, the determining the attribute relationships comprising iteratively performing a leveling operation for each episode pair in the transition list, the leveling operation to determine a parent episode for each child episode of each episode pair in the transition list at a particular association level.

28. The computer-implemented method of claim 27, the leveling operation comprising starting with identity episode pairs in the transition list and add each episode pair to a table, evaluating each episode pair at each association level, and increasing by association level until no episode pair remain in the transition list.

29. The computer-implemented method of claim 27, the leveling operation comprising determining a number of times each episode is a child episode at the particular level, and calculating a weighted level value for each episode pair used to determine the attribute relationships between episodes, the attribute relationships comprising cost associations between the episodes.

30. A system, comprising:

a storage device;

an interface coupled with the storage device;

processing circuitry coupled with the storage device and interface;

memory coupled with the processing circuitry, the storage device, and the interface;

a candidate component having instructions storable in the memory and operable on the processing circuitry, the candidate component to:

receive episode information for a patient from a storage device via one or more links, the episode information comprising a plurality of episodes associated with the patient, each of the plurality of episodes is a specific instance of a medical condition, and generate a candidate episode pairs list comprising a plurality of candidate episode pairs by:

performing a Cartesian merge of the plurality of episodes, and comparing each of the candidate episode pairs with association information defining related medical conditions, each of the candidate episode pairs having a different association level and each of the candidate episode pairs define a parent-child relationship, each of the association levels define a relative strength between episodes in each of the candidate episode pairs;

a transition component having instructions storable in the memory and operable on the processing circuitry, the transition component to generate a transition list comprising episode pairs from the plurality of candidate episode pairs in the candidate episode pairs list; and a leveling component having instructions storable in the memory and operable on the processing circuitry to determine attribute relationships between the plurality of episodes for the patient based on episode pairs in the transition list, the attribute relationships used to attribute items between the plurality of episodes.

* * * * *